US012357713B2

(12) United States Patent
Fritchie et al.

(10) Patent No.: US 12,357,713 B2
(45) Date of Patent: Jul. 15, 2025

(54) INDUCTIVE HEATING SYSTEMS AND METHODS OF CONTROLLING THE SAME TO REDUCE BIOLOGICAL CARRYOVER

(71) Applicant: Abbott Laboratories, Abbott Park, IL (US)

(72) Inventors: Patrick Fritchie, Southlake, TX (US); Pathik Soni, Chicago, IL (US); Lei Qiao, Addison, TX (US); Dustin House, Carrollton, TX (US); Lyle Yarnell, Richardson, TX (US); Edna Prieto-Ballengee, Dallas, TX (US); Cathy Forsythe, Beach Park, IL (US); Michael Shawn Murphy, Allen, TX (US); Andrew Fischer, Euless, TX (US); Akanksha Sharma, Ann Arbor, MI (US); Joseph Esposito, Kenosha, WI (US); Matt Effinger, Paddock Lake, WI (US); Michael Futer, Grand Prairie, TX (US)

(73) Assignee: ABBOTT LABORATORIES, Abbott Park, IL (US)

( * ) Notice: Subject to any disclaimer, the term of this patent is extended or adjusted under 35 U.S.C. 154(b) by 980 days.

(21) Appl. No.: 17/375,737

(22) Filed: Jul. 14, 2021

(65) Prior Publication Data

US 2021/0338856 A1 Nov. 4, 2021

Related U.S. Application Data

(63) Continuation of application No. 15/851,199, filed on Dec. 21, 2017, now Pat. No. 11,065,352.

(Continued)

(51) Int. Cl.
*H05B 6/06* (2006.01)
*A61L 2/04* (2006.01)

(Continued)

(52) U.S. Cl.
CPC .................. *A61L 2/04* (2013.01); *A61L 2/24* (2013.01); *H05B 6/06* (2013.01); *H05B 6/101* (2013.01);

(Continued)

(58) Field of Classification Search
CPC .......... A61L 2/04; A61L 2/24; A61L 2202/14; H05B 6/06; H05B 6/101; H05B 6/108; H05B 6/14; H05B 6/40

(Continued)

(56) References Cited

U.S. PATENT DOCUMENTS

| | | | | |
|---|---|---|---|---|
| 3,823,297 A * | 7/1974 | Cunningham | ........ | H02M 7/525 219/626 |
| 4,327,268 A | 4/1982 | Frank | | |

(Continued)

FOREIGN PATENT DOCUMENTS

| | | |
|---|---|---|
| CN | 1454318 A | 11/2003 |
| CN | 2629702 Y | 8/2004 |

(Continued)

OTHER PUBLICATIONS

National Intellectual Property Administration, P.R. China, "Notification to Grant Patent Right for Invention," issued in connection with Chinese Patent No. 201780087034.0, dated Mar. 23, 2022, 4 pages (includes English translation).

(Continued)

*Primary Examiner* — Quang T Van
(74) *Attorney, Agent, or Firm* — HANLEY, FLIGHT & ZIMMERMAN, LLC

(57) ABSTRACT

Inductive heating systems and method of controlling the same to reduce biological carryover are disclosed herein. An example system includes an induction heater including a tank circuit, the tank circuit including a work coil and a sense coil. The sense coil is to detect a magnetic field generated by the work coil and to output signals in response (Continued)

to the detection. The example system includes a controller to cause the tank circuit to oscillate at a resonant frequency in response to the signals and a power drive unit in communication with the controller and the induction heater. The power drive unit is to adjust power provided to the induction heater in response to the controller driving the tank circuit to oscillate at the resonant frequency.

14 Claims, 9 Drawing Sheets

Related U.S. Application Data

(60) Provisional application No. 62/438,250, filed on Dec. 22, 2016.

(51) Int. Cl.
*A61L 2/24* (2006.01)
*H05B 6/10* (2006.01)
*H05B 6/14* (2006.01)
*H05B 6/40* (2006.01)

(52) U.S. Cl.
CPC ............... *H05B 6/108* (2013.01); *H05B 6/14* (2013.01); *H05B 6/40* (2013.01); *A61L 2202/14* (2013.01)

(58) Field of Classification Search
USPC ....... 219/600, 607, 608, 626, 627, 629, 630, 219/635, 643, 647, 650, 663, 664, 665, 219/666, 667, 672
See application file for complete search history.

(56) References Cited

U.S. PATENT DOCUMENTS 4,492,840 A 1/1985 Lex
4,608,472 A 8/1986 Kato
5,178,019 A 1/1993 Keiter
5,434,389 A 7/1995 Griebel
5,476,634 A 12/1995 Bridges et al.
5,765,490 A 6/1998 Colin et al.
5,882,594 A 3/1999 Kawaguchi et al.
5,965,086 A 10/1999 Rose et al.
6,379,631 B1 4/2002 Wu
6,582,659 B1 6/2003 Murata
6,627,163 B1 9/2003 Awakowicz et al.
6,632,287 B1 10/2003 Colin et al.
6,692,693 B2 2/2004 Wu
6,734,405 B2 5/2004 Centanni et al.
6,756,223 B2 6/2004 Roberts et al.
6,759,017 B2 7/2004 Wu et al.
6,906,296 B2 6/2005 Centanni et al.
6,930,292 B1 8/2005 Winther et al.
6,967,315 B2 11/2005 Centanni et al.
7,017,594 B2 3/2006 Kurunczi
7,094,314 B2 8/2006 Kurunczi
7,367,344 B2 5/2008 Kurunczi
7,446,288 B2 11/2008 Boege et al.
7,507,369 B2 3/2009 Lu
7,687,045 B2 3/2010 Lu
7,781,708 B2 8/2010 Wallace et al.
7,858,908 B2 12/2010 Wallace et al.
7,927,557 B2 4/2011 Dieras et al.
7,939,016 B2 5/2011 Lu
8,092,643 B2 1/2012 Kurunczi
8,092,644 B2 1/2012 Kurunczi
8,115,147 B2 2/2012 Thomas et al.
8,366,871 B2 2/2013 Kurunczi
8,444,919 B2 5/2013 Erickson
8,591,807 B2 11/2013 Berentsveig et al.
8,591,808 B2 11/2013 Berentsveig et al.
8,658,089 B2 2/2014 Berentsveig et al.
8,974,737 B2 3/2015 Erickson
9,011,786 B2 4/2015 Hemphill et al.
9,073,094 B2 7/2015 Weston et al.
9,075,042 B2 7/2015 Cook et al.
9,081,001 B2 7/2015 Cook et al.
9,101,678 B2 8/2015 Hegg et al.
9,138,005 B2 9/2015 Berentsveig et al.
9,162,259 B2 10/2015 Reidt et al.
9,192,164 B2 11/2015 Berentsveig et al.
9,213,043 B2 12/2015 Cook et al.
9,222,665 B2 12/2015 Halas et al.
9,241,491 B2 1/2016 Berentsveig et al.
9,522,205 B2 12/2016 Ahiska
9,545,458 B2 1/2017 Halas et al.
9,616,426 B2 4/2017 Dulaff
9,625,465 B2 4/2017 Cook et al.
9,686,824 B2 6/2017 Weston et al.
9,837,862 B2 12/2017 Sherman et al.
9,901,651 B2 2/2018 Finke et al.
9,950,824 B2 4/2018 Miyahara et al.
9,974,872 B2 5/2018 Weston et al.
10,399,086 B2 9/2019 Waldenmaier et al.
10,411,510 B2 9/2019 Sherman et al.
10,561,793 B2 2/2020 Finke et al.
10,603,439 B2 3/2020 Strader
10,688,543 B2 6/2020 Thompson et al.
11,065,352 B2 7/2021 Fritchie et al.
11,452,787 B2 9/2022 Weston et al.
2003/0170686 A1 9/2003 Hoet
2004/0022665 A1 2/2004 Lu
2007/0026442 A1 2/2007 Calasso et al.
2009/0291018 A1 11/2009 Wallace et al.
2010/0198220 A1 8/2010 Boudreaux et al.
2010/0282739 A1 11/2010 Wallace et al.
2011/0117202 A1 5/2011 Bourke, Jr. et al.
2011/0139189 A1 6/2011 Reidt et al.
2011/0211989 A1 9/2011 Hemphill et al.
2011/0222889 A1 9/2011 Tabuchi
2012/0019316 A1 1/2012 Hattersley et al.
2012/0156102 A1 6/2012 Halas et al.
2012/0251386 A1 10/2012 Wootton et al.
2013/0167872 A1 7/2013 Weston et al.
2014/0037495 A1 2/2014 Ahiska et al.
2014/0119985 A1 5/2014 Berg et al.
2014/0119986 A1 5/2014 Finke et al.
2014/0158678 A1 6/2014 Thomann et al.
2014/0183178 A1 7/2014 Guichard et al.
2015/0073352 A1 3/2015 Finke et al.
2015/0073353 A1 3/2015 Strader
2015/0224503 A1 8/2015 Dulaff
2015/0266024 A1 9/2015 Leland
2015/0296571 A1 10/2015 Holcomb
2015/0312968 A1 10/2015 Weston et al.
2016/0228590 A1 8/2016 Waldenmaier et al.
2017/0246328 A1 8/2017 Weston et al.
2018/0132960 A1 5/2018 Scibilia et al.
2018/0193498 A1 7/2018 Fritchie et al.
2018/0264149 A1 9/2018 Weston et al.
2019/0321500 A1 10/2019 Anderson et al.

FOREIGN PATENT DOCUMENTS

CN 2704368 6/2005
CN 1668143 A 9/2005
CN 1802044 A 7/2006
CN 1986012 A 6/2007
CN 102193447 A 9/2011
DE 2911565 A1 9/1980
DE 4428228 A1 2/1996
EP 0121980 A2 10/1984
EP 0727228 A1 8/1996
EP 3101779 12/2016
FR 2730638 A1 8/1996
IN 101389280 A 3/2009
JP S60143587 7/1985
JP H07201460 A 8/1995
JP H11162623 A 6/1999
JP 3704425 B2 10/2005
JP 2007078825 A 3/2007

(56) References Cited

FOREIGN PATENT DOCUMENTS

| | | | |
|---|---|---|---|
| JP | 2008119417 | A | 5/2008 |
| JP | 2009158394 | A | 7/2009 |
| JP | 2010246509 | A | 11/2010 |
| JP | 2015065091 | | 4/2015 |
| WO | 9013318 | A1 | 11/1990 |
| WO | 03049530 | A2 | 6/2003 |
| WO | 2006006946 | | 1/2006 |
| WO | 2006121838 | A2 | 11/2006 |
| WO | 2011089900 | A1 | 7/2011 |
| WO | 2012040868 | A2 | 4/2012 |
| WO | 2014035804 | A1 | 3/2014 |

OTHER PUBLICATIONS

United States Patent and Trademark Office, "Notice of Allowance and Fee(s) Due," issued in connection with U.S. Appl. No. 15/984,741, dated Mar. 30, 2022, 6 pages.

United States Patent and Trademark Office, "Corrected Notice of Allowability," issued in connection with U.S. Appl. No. 15/984,741, dated May 11, 2022, 3 pages.

Chinese Patent Office, "First Office Action," issued in connection with Chinese Patent Application No. 202110075918.2, dated Apr. 28, 2022, 11 pages (included English translation).

United States Patent and Trademark Office, "Corrected Notice of Allowability," issued in connection with U.S. Appl. No. 15/984,741, dated Jul. 7, 2022, 3 pages.

European Patent Office, "Communication pursuant to Article 94(3) EPC," issued in connection with European Patent Application No. 17842406.5, dated Jun. 9, 2022, 5 pages.

Japanese Patent Office, "Office Action," issued in connection with Japanese Patent Application No. 2021-113291, dated Jul. 12, 2022, 9 pages (English translation provided).

United States Patent and Trademark Office, "Corrected Notice of Allowability," issued in connection with U.S. Appl. No. 15/984,741, dated Aug. 17, 2022, 3 pages.

United States Patent and Trademark Office, "Advisory Action," issued in connection with U.S. Appl. No. 15/984,741, dated Sep. 3, 2020, 3 pages.

European Patent Office, "Communication Pursuant to Article 94(3) EPC," issued in connection with European Patent Application No. 17160886.2 dated Apr. 25, 2023, 4 pages.

European Patent Office, "Communication Pursuant to Article 94(3) EPC," issued in connection with European Patent Application No. 17842406.5, dated Nov. 29, 2023, 5 pages.

European Patent Office, "Summons to Attend Oral Proceedings Pursuant to Rule 115(1) EPC," issued in connection with European Patent Application No. 17160886.2, dated Nov. 27, 2023, 6 pages.

European Patent Office, "Communication pursuant to Article 94(3) EPC," issued in connection with European Patent Application No. 17160886.2, dated Oct. 10, 2022, 4 pages.

Japanese Patent Office, "Decision to Grant a Patent," issued in connection with Japanese Patent Application No. 2021-113291, dated Nov. 25, 2022, 5 pages. (English translation included).

National Intellectual Property Administration, P.R. China, "Notification to Grant Patent Right for Invention," issued in connection with Chinese Patent Application No. 202110075918.2, dated Nov. 30, 2022, (English translation included).

European Patent Office, "Communication pursuant to Article 94(3) EPC," issued in connection with European Patent Application No. 17 160 886.2, dated Nov. 13, 2024, 5 pages.

International Searching Authority, "Invitation to Pay Additional Fees and Partial International Search," Issued in connection with corresponding PCT application No. PCT/US2012/070807, dated Apr. 18, 2013, 8 pages.

International Searching Authority, "International Search Report and Written Opinion of the International Searching Authority," issued in connection with application No. PCT/US2012/070807, dated Aug. 30, 2013, 20 pages.

International Bureau, "International Preliminary Report on Patentability," issued in connection with application no. PCT/US2012/070807, dated Jul. 10, 2014, 14 pages.

European Patent Office, "Extended European Search Report," issued in connection with European Patent Application No. 17160886.2, dated Aug. 3, 2017, 8 pages.

European Patent Office, "Communication Under Article 71(3) EPC," issued in connection with European Patent Application No. 12813208.1, dated May 25, 2016, 43 pages.

State Intellectual Property Office of China, "Second Office Action," issued in connection with Chinese Patent Application No. 201280070734.6, dated Aug. 31, 2016, 10 pages.

European Patent Office, "Invitation pursuant to Rule 137(4)," issued in connection with European Patent Application No. 12813208.1, dated Oct. 27, 2016, 3 pages.

European Patent Office, "Invitation Pursuant to Rule 137(4) EPC", issued in connection with European Patent Application No. 12813208.1 dated Aug. 25, 2015, 2 pages.

State Intellectual Property Office of China, "Notification to Grant Patent Right for Invention," issued in connection with application No. 201280070734.6, dated Mar. 3, 2017, 4 pages (includes English translation).

State Intellectual Property Office of China, "Notification of First Office Action and Search Report," Issued in connection with Chinese Patent Application No. 201280070734.6, dated Nov. 2, 2015, 15 pages.

United States Patent and Trademark Office, "Office Action", issued in connection with U.S. Appl. No. 13/721,931, dated Jun. 2, 2014, 9 pages.

United States Patent and Trademark Office, "Office Action", issued in connection with U.S. Appl. No. 13/721,931, dated Sep. 11, 2014, 26 pages.

United States Patent and Trademark Office, "Notice of Allowance", issued in connection with U.S. Appl. No. 13/721,931, dated Mar. 4, 2015, 9 pages.

United States Patent and Trademark Office, "Notice of Allowance," issued in connection with U.S. Appl. No. 14/791,964, dated Feb. 14, 2017, 26 pages.

United States Patent and Trademark Office, "Non-final Office Action," issued in connection with U.S. Appl. No. 14/791,964, dated Jun. 17, 2016, 29 pages.

United States Patent and Trademark Office, "Corrected Notice of Allowability," issued in connection with U.S. Appl. No. 14/791,964, dated May 23, 2017, 7 pages.

United States Patent and Trademark Office, "Office Action," issued in connection with U.S. Appl. No. 15/593,955, dated Jul. 3, 2017, 8 pages.

United States Patent and Trademark Office, "Notice of Allowance," issued in connection with U.S. Appl. No. 15/593,955, dated Jan. 22, 2018, 34 pages.

The International Bureau, "International Preliminary Report on Patentability," issued in connection with application No. PCT/US2017/067890, dated Jun. 25, 2019, 10 pages.

International Searching Authority, "International Search Report," issued in connection with International Application No. PCT/US2017/067890, dated Apr. 25, 2018, 16 pages.

United States Patent and Trademark Office, "Final Office Action", issued in connection with U.S. Appl. No. 15/984,741, dated Jun. 25, 2020, 9 pages.

National Intellectual Property Administration, P.R. China, "First Office Action," issued in connection with Chinese Patent Application No. 201710352255.8, dated Jan. 15, 2020, 17 pages (includes English translation).

United States Patent and Trademark Office, "Non-Final Office Action," issued in connection with U.S. Appl. No. 15/984,741, dated Mar. 5, 2020, 8 pages.

Chinese Patent Office, "Second Office Action," issued in connection with Chinese Patent Application No. 201710352255.8, dated Jul. 24, 2020, 7 pages (includes English translation).

United States Patent and Trademark Office, "Final Office Action," issued in connection with U.S. Appl. No. 15/984,741 dated Oct. 7, 2020, 12 pages.

(56) References Cited

OTHER PUBLICATIONS

Japanese Patent Office, "Office Action," issued in connection with Japanese Patent Application No. 2019-534265, dated Sep. 8, 2020, 8 pages (includes English translation).
Chinese Patent Office, "Notification to Grant Patent Right for Invention," issued in connection with Chinese Patent Application No. 201710352255.8, dated Nov. 5, 2020, 4 pages (includes English translation).
United States Patent and Trademark Office, "Advisory Action," issued in connection with U.S. Appl. No. 15/984,741 dated Dec. 24, 2020, 3 pages.
European Patent Office, "Communication Pursuant to Article 94(3) EPC," issued in connection with European Patent Application No. 17842406.5, dated Mar. 24, 2021, 5 pages.
The State Intellectual Property Office of Peoples Republic of China, "First Office Action," issued In connection with Chinese Patent Application No. 201780087034, dated Mar. 5, 2021, 34 pages (includes English translation).
European Patent Office, "Communication Pursuant to Article 94(3) EPC," issued in connection with European Patent Application No. 17160886.2, dated May 18, 2021, 4 pages.
Japanese Patent Office, "Final Decision to Allowance," issued in connection with Japanese Patent Application No. 2019-534265, dated Apr. 27, 2021, 4 pages (includes English translation).
United States Patent and Trademark Office, "Non-Final Office Action," issued in connection with U.S. Appl. No. 15/851,199, dated Apr. 6, 2020, 10 pages.
United States Patent and Trademark Office, "Restriction," issued in connection with U.S. Appl. No. 15/851,199, dated Jan. 10, 2020, 6 pages.
United States Patent and Trademark Office, "Final Office Action," issued in connection with U.S. Appl. No. 15/851,199 on Nov. 17, 2020, 13 pages.
United States Patent and Trademark Office, "Notice of Allowance," issued in connection with U.S. Appl. No. 15/851,199, dated on Mar. 17, 2021, 8 pages.
United States Patent and Trademark Office, "Corrected Notice of Allowance," issued in connection with U.S. Appl. No. 15/851,199, dated May 18, 2021, 2 pages.
United States Patent and Trademark Office, "Supplemental Notice of Allowance," issued in connection with U.S. Appl. No. 15/851,199, dated May 27, 2021, 2 pages.
United States Patent and Trademark Office, "Supplemental Notice of Allowance," issued in connection with U.S. Appl. No. 15/851,199, dated on Jun. 24, 2021, 2 pages.
United States Patent and Trademark Office, "Non-Final Office Action," issued in connection with U.S. Appl. No. 15/984,741, dated Jul. 20, 2021, 18 pages.
European Patent Office, "Intention to Grant," issued in connection with European Patent Application No. 12813208.1, dated Aug. 6, 2021, 8 pages.
Chinese Patent Office, "Second Office Action," issued in connection with Chinese Patent Application No. 201780087034.0, dated Sep. 24, 2021, 3 pages.
United States Patent and Trademark Office, "Notice of Allowance," issued in connection with U.S. Appl. No. 15/984,741, dated Dec. 15, 2021, 8 pages.
United States Patent and Trademark Office, "Notice of Allowance and Fee(s) Due," issued in connection with U.S. Appl. No. 17/951,837, dated Apr. 9, 2024, 8 pages.
The State Intellectual Property Office of the People's Republic of China, "First Office Action and First Search," issued in connection with Application No. 202210633653.8, dated Jul. 15, 2024, 20 pages [English Translation Included].
European Patent Office, "Result of Consultation," issued in connection with European Patent Application No. 17 160 886.2, dated Sep. 30, 2024, 3 pages.
Japan Patent Office, "Decision of Refusal," issued in connection with Japanese Patent Application No. 2022-201866, dated Aug. 6, 2024, 13 pages. [English Translation Included].
The State Intellectual Property Office of People's Republic of China, "First Office Action and First Search," issued in connection with Chinese Patent Application No. 202310125668.8, dated Jul. 25, 2024, 14 pages. [English Translation Included].
Japan Patent Office, "Notice of Reasons for Refusal," issued in connection with Japanese Patent Application No. 2022-201866, dated Feb. 27, 2024, 10 pages. [English Translation Included].
The State Intellectual Property of People's Republic of China, "Notification to Grant Patent Right for Invention," issued in connection with Chinese patent Application No. 202310125668.8, dated Mar. 3, 2025, 3 pages. [English Translation Included].
Japanese Patent Office, "Decision to Grant a Patent ," issued in connection with Japanese Patent Application No. 2022-201866, dated Mar. 4, 2025, 5 pages. [English Translation Included].

* cited by examiner

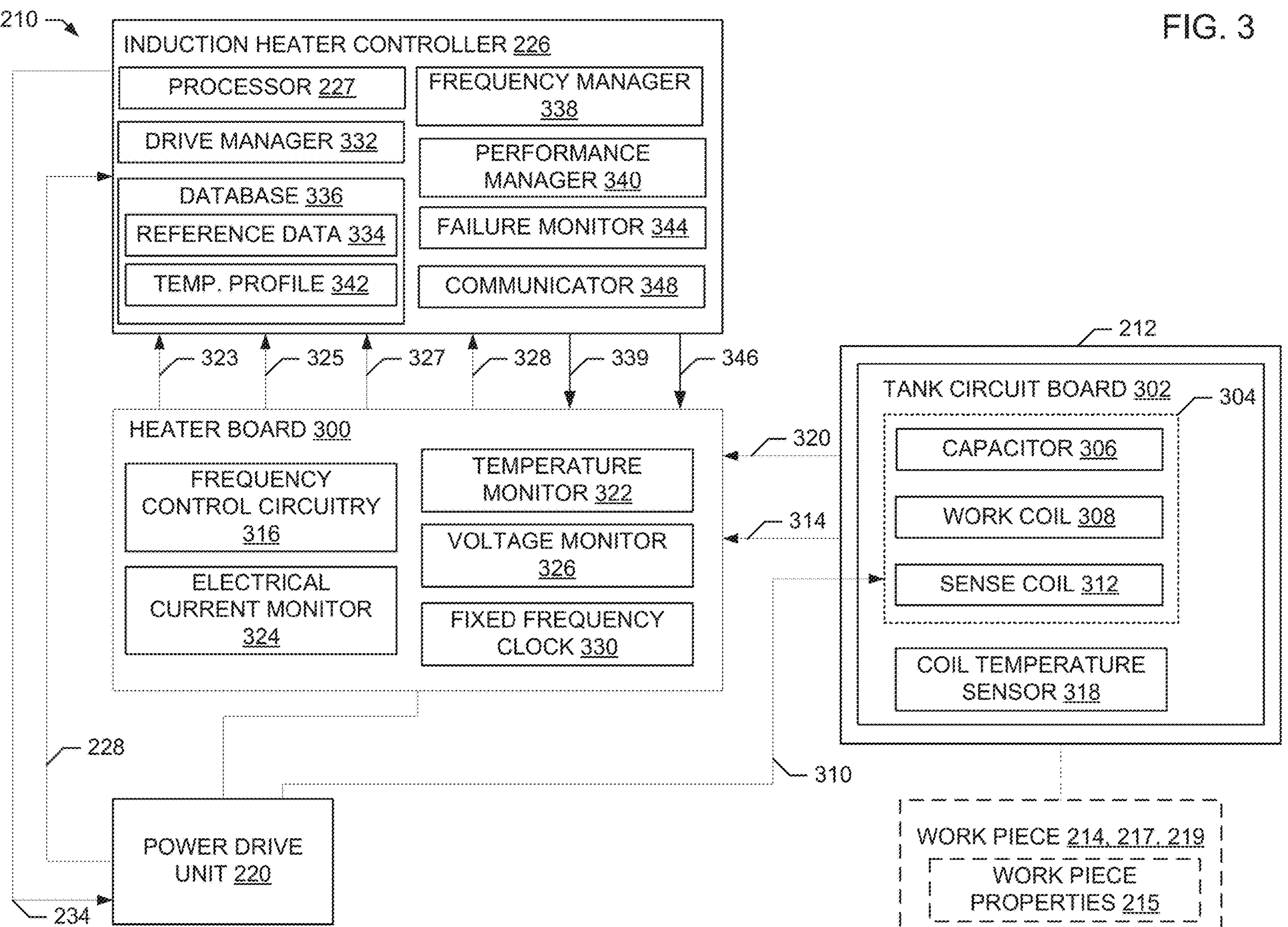
FIG. 3
210
INDUCTION HEATER CONTROLLER 226
PROCESSOR 227
FREQUENCY MANAGER 338
DRIVE MANAGER 332
PERFORMANCE MANAGER 340
DATABASE 336
REFERENCE DATA 334
TEMP. PROFILE 342
FAILURE MONITOR 344
COMMUNICATOR 348
323
325
327
328
339
346
HEATER BOARD 300
FREQUENCY CONTROL CIRCUITRY 316
ELECTRICAL CURRENT MONITOR 324
TEMPERATURE MONITOR 322
VOLTAGE MONITOR 326
FIXED FREQUENCY CLOCK 330
320
314
212
TANK CIRCUIT BOARD 302
304
CAPACITOR 306
WORK COIL 308
SENSE COIL 312
COIL TEMPERATURE SENSOR 318
228
310
POWER DRIVE UNIT 220
234
WORK PIECE 214, 217, 219
WORK PIECE PROPERTIES 215

INDUCTIVE HEATING SYSTEMS AND METHODS OF CONTROLLING THE SAME TO REDUCE BIOLOGICAL CARRYOVER

RELATED APPLICATIONS

This patent arises from a continuation of U.S. patent application Ser. No. 15/851,199, now U.S. Pat. No. 11,065,352, which was filed on Dec. 21, 2017. U.S. patent application Ser. No. 15/851,199 claims priority to U.S. Provisional Patent Application No. 62/438,250, which was filed on Dec. 22, 2016. U.S. patent application Ser. No. 15/851,199 and U.S. Provisional Patent Application No. 62/438,250 are hereby incorporated herein by reference in their entireties. Priority to U.S. patent application Ser. No. 15/851,199 and U.S. Provisional Patent Application No. 62/438,250 is hereby claimed.

FIELD OF THE DISCLOSURE

This disclosure relates generally to medical diagnostic instruments and, more particularly, to inductive heating systems and methods of controlling the same to reduce biological carryover.

BACKGROUND

Aspiration and dispense devices such as pipettor probes are used with automated medical diagnostic instruments to aspirate and/or dispense fluids such as biological samples (e.g., serum, urine) and/or reagents as part of diagnostic testing procedures. Aspiration and dispense devices can be reused to reduce waste and operational costs. However, reusing aspiration and dispense devices increases the probability of introducing biological carryover and/or contamination into subsequent tests.

BRIEF DESCRIPTION OF THE DRAWINGS

FIG. 3 is a block diagram of an example induction heater station of the example system of FIG. 2.

The figures are not to scale. Instead, to clarify multiple layers and regions, the thickness of the layers may be enlarged in the drawings. Wherever possible, the same reference numbers will be used throughout the drawing(s) and accompanying written description to refer to the same or like parts.

DETAILED DESCRIPTION

Figure 1:
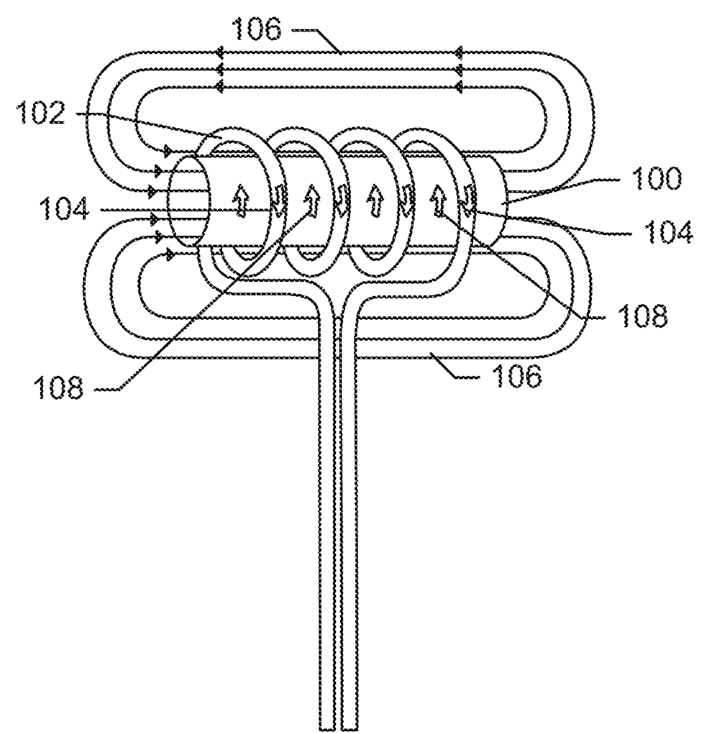
FIG. 1 is a schematic illustration of electromagnetic induction.

Automated medical diagnostic instruments such as clinical chemistry analyzers can be used to analyze a biological sample (e.g., serum, urine) by performing one or more tests on the sample, such as an immunoassay. An aspiration and dispense device such as a pipettor probe may be used with the diagnostic instrument as part of, for example, an automated pipetting system for transporting fluids within the instrument such as the sample, one or more reagents, etc. For example, an aspiration and dispense device can be used to deliver and/or remove fluids from reaction vessels of the instrument, move fluids between vessels, mix fluids, etc.

During use, at least a portion of the interior and/or exterior surfaces of the aspiration and dispense device are exposed to the fluids that the aspiration and dispense device transports. In some examples, residual materials associated with the sample and/or reagent, such as proteins or viral materials, may remain on the interior and/or the exterior surfaces of the aspiration and dispense device. As a result, subsequent use of the aspiration and dispense device can result in carryover of the sample or the reagent, or the transfer of the sample or the reagent into another sample or reagent. Thus, reuse of the aspiration and dispense device can contaminate the sample and/or the regent exposed to the aspiration and dispense device in connection with subsequent uses of the device. The aspiration and dispense device can be cleaned in an effort to reduce carryover and/or contamination by sterilizing the device using, for example, heat.

Example systems, methods, and apparatus disclosed herein use electromagnetic inductive heating to clean a work piece such as an aspiration and dispense device. Examples disclosed herein include an induction heater that can be integrated in and implemented by an automated diagnostic instrument, such as a clinical chemistry analyzer, an immunoassay analyzer, etc. In some examples disclosed herein, the instrument in which the induction heater is integrated provides power to the induction heater, is used to control one or more settings of the induction heater via a graphical user interface, etc. In some disclosed examples, the induction heater includes an induction heating circuit including an electrically conducting media, such as a coil. An electrical current is provided to the electrically conducting media, which induces an electromagnetic field. In disclosed examples, the work piece is disposed proximate to the electrically conducting media (e.g., inserted in an opening in the coil) and heated via the magnetic field. In disclosed examples, heating the aspiration and dispense device substantially removes and/or alters one or more properties of the material remaining on the aspiration and dispense device so as to substantially reduce the probability of carryover and/or contamination with subsequent use of the aspiration and dispense device.

In some disclosed examples, a wash fluid is applied to the work piece before, during, and/or after inductively heating the work piece to rinse the biological and/or chemical materials from the surfaces of the device. Some disclosed examples include a wash cup to collect the wash fluid. In some disclosed examples, the electrically conducting media is disposed proximate to the wash cup, and in some examples, is removably secured to a portion of the wash cup to facilitate collection of the wash fluid during inductive heating of the work piece.

In examples disclosed herein, the induction heating circuit includes tank circuit including a first coil to serve as an electrically inducting media for heating the work piece. In some disclosed examples, a second coil is wound around the first coil to sense an oscillating magnetic field generated by the first coil and to synchronize electrical current provided to the tank circuit with current already flowing through first coil. In examples disclosed herein, signals corresponding to the oscillating magnetic field generated by the first coil are dynamically detected by the second coil. The signals are used to drive the electrical current provided to the tank circuit such that the tank circuit is driven at its resonant frequency rather than a fixed frequency. Driving the tank circuit at its resonant frequency reduces energy losses and provides for an increased amount of energy to be transferred to the aspiration and dispense device heated by the first coil as compared to driving the tank circuit at a fixed frequency. Thus, disclosed examples improve efficiency of the inductive heating of the aspiration and dispense device. Driving the tank circuit to resonate at its natural frequency also compensates for manufacturing variability with respect to components such as coils and capacitors. Driving the tank circuit to resonate at its natural frequency also accommodates dynamic load variabilities with respect to changes in the resonant frequency of the tank circuit due to the introduction of work pieces having different diameters, skin thickness, etc. into the magnetic field.

In some disclosed examples, the electrically conducting media of the induction heating circuit (e.g., the coil) is coated with one or more materials to prevent corrosion from biological and chemical interactions between the work piece, the wash fluid, and the electrically conducting media. Some disclosed examples detect and/or predict failure of one or more components of the induction heater by monitoring performance data of the heater such as voltage, current, and frequency. Also, some disclosed examples include a heat sink to reduce a risk of overheating of the coil and a printed circuit board on which components such as capacitors of the tank circuit are mounted. Thus, disclosed examples provide stable and reliable means for inductively heating and aspiration and dispense device.

An example system disclosed herein includes an induction heater including a tank circuit. The example system includes a controller to drive the tank circuit to selectively oscillate at a resonant frequency for the tank circuit to inductively heat a work piece disposed proximate to the tank circuit.

In some examples, the controller is to drive the tank circuit to selectively oscillate at the resonant frequency based on a property of the work piece.

In some examples, the controller is to drive the tank circuit to selectively oscillate between the resonant frequency and a fixed frequency.

In some examples, the tank circuit includes a work coil and a sense coil. In such examples, the sense coil is to be wound around the work coil.

In some examples, the controller is to drive the tank circuit to oscillate at the resonant frequency based on a signal generated by the sense coil.

In some examples, the system further includes a heat sink coupled to the induction heater.

In some examples, the system further includes a shield including a thermally conductive material coupled to the induction heater.

In some examples, the tank circuit includes a work coil, the work coil to be disposed in a wash cup. In some such examples, the work piece is to be exposed to fluid during the inductive heating. In some such examples, the fluid is to undergo a phase change during the inductive heating.

In some examples, the controller is to access at least one of temperature data, current data, or voltage data from the induction heater. In such examples, the controller is to predict a performance condition of the induction heater based on the data.

In some examples, the work piece includes a first portion and a second portion. In such examples, the controller to selectively adjust a heat setting at the tank circuit for the first portion and the second portion. In some such examples, the controller is to adjust the heat setting for the first portion based on a first temperature profile for the first portion and adjust the heat setting for the second portion based on a second temperature profile for the second portion.

An example method disclosed herein includes providing, by executing an instruction with a processor, a current to an induction heater, the induction heater including a tank circuit. The example method includes driving, by executing an instruction with the processor, the tank circuit to selectively oscillate at a resonant frequency for the tank circuit. The example method includes inductively heating a work piece disposed proximate to the tank circuit.

In some examples, the driving of the tank circuit to selectively oscillate at the resonant frequency is to be based on a property of the work piece.

An example tangible computer-readable medium disclosed herein includes instructions that, when executed, cause a processor to at least provide a current to an induction heater, the induction heater including a tank circuit. The instructions cause the processor to drive the tank circuit to selectively oscillate at a resonant frequency for the tank circuit to inductively heat a work piece disposed proximate to the tank circuit.

In some examples, the instructions, when executed, further cause the processor to drive the tank circuit to selectively oscillate at the resonant frequency based on a property of the work piece.

In some examples, the instructions, when executed, further cause the processor to drive the tank circuit to selectively oscillate between the resonant frequency and a fixed frequency.

In some examples, the work piece includes a first portion and a second portion, and the instructions, when executed, further cause the processor to selectively adjust a heat setting at the tank circuit for the first portion and the second portion.

In some examples, the instructions, when executed, further cause the processor to adjust the heat setting for the first portion based on a first temperature profile for the first portion and adjust the heat setting for the second portion based on a second temperature profile for the second portion.

Turning now to the figures, FIG. 1 is a schematic illustration of electromagnetic induction. As shown in FIG. 1, at least a portion of a work piece 100 to be heated (e.g., an aspiration and dispense device) is removably disposed in an electrically conducting media such as, for example, a coil 102. In the example of FIG. 1, the work piece 100 includes a metal. An alternating current is provided to the coil 102

(e.g., from a current source) and flows through the coil 102, as represented by arrows 104 in FIG. 1. The alternating current flowing through the coil 102 induces a magnetic field 106 in an area around the coil 102. The magnetic field 106 induces eddy currents the work piece 100, as represented by the arrows 108 in FIG. 1. The eddy currents generate localized heat that raises the temperature of the work piece 100 without direct contact between the work piece 100 and the coil 102. In examples where the work piece 100 is an aspiration and dispense device, the heat can affect properties of one or more materials (e.g., residual biological materials) on the interior and/or exterior surface of the work piece 100 to enable the materials to be removed or altered and the work piece 100 to be cleaned.

Figure 2:
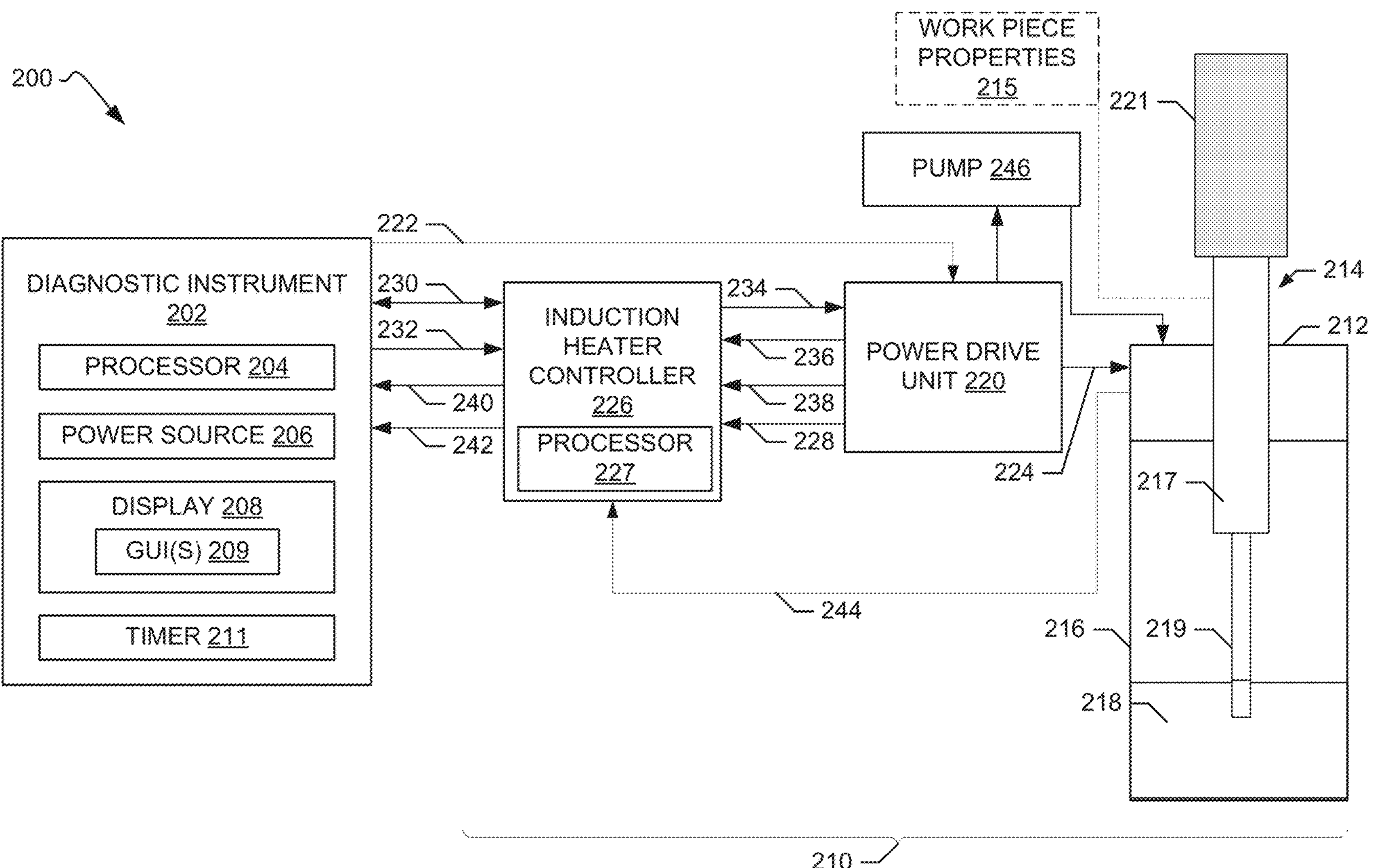
FIG. 2 is a block diagram of an example system for inductively heating a work piece constructed in accordance with teachings disclosed herein.

FIG. 2 is a block diagram of an example system 200 to reduce biological carryover via inductive heating. The example system 200 includes a diagnostic instrument 202. The diagnostic instrument 202 can be, for example, clinical chemistry analyzer, an immunoassay analyzer, etc. The example diagnostic instrument 202 includes a processor 204 to control one or more functions performed by the instrument 202, such as manipulating test samples, performing readings of the test samples, positioning reaction vessels, delivering fluids to and/or removing fluids from the reaction vessels, etc. The example diagnostic instrument 202 includes a power source 206. The power source 206 can include, for example, a battery, an electrical outlet, etc. The example diagnostic instrument 202 includes a display 208. The display 208 can present one or more graphical user interfaces (GUIs) 209 to a user of the diagnostic instrument 202 to, for example, receive user inputs via the GUI(s) 209, display analysis results via the GUI(s) 209, etc. The diagnostic instrument 202 can include a timer 211 to monitor, trigger, or more generally provide timing control of one or more functions performed by the diagnostic instrument 202 with respect to analyzing a sample.

In the example system 200 of FIG. 2, the diagnostic instrument 202 includes an induction heater control station 210. The example induction heater control station 210 includes an induction heater 212 to clean or sterilize a work piece 214 (e.g., the work piece 100 of FIG. 1) via inductive heating as substantially disclosed in connection with FIG. 1. The work piece 214 can include an aspiration and dispense device that may be used to perform one or more functions with respect to experiments and/or analyses performed by the diagnostic instrument 202, such as transporting a biological sample, delivering a reagent, etc. As a result of the use of the work piece 214 with the diagnostic instrument 202, the work piece 214 may include biological and/or chemical material residue on one or more surfaces of the work piece 214 such that re-use of the work piece 214 could contaminate other samples and/or reagents.

The work piece 214 can include one or more portions having different properties 215 with respect to, for example, skin thickness, diameter, cross-section shape, material, etc. The properties 215 of the work piece 214 can affect magnetic properties of the work piece 214 with respect to heating the work piece 214 via a magnetic field. For example, as illustrated in FIG. 2, the work piece 214 can include a first portion 217 having a first diameter and a second portion 219 having a second diameter smaller than the first diameter. In some examples, the work piece 214 is moved relative to the induction heater 212 via, for example, a robotic arm 221 of the diagnostic instrument 202 so as to selectively heat and clean the first portion 217 and the second portion 219 of the work piece 214. The work piece 214 can include additional or fewer portions than illustrated in FIG. 2. In some examples, the work piece 214 is a probe including an opening defined by and extending through the portions 217, 219 of the work piece.

In the example of FIG. 2, the induction heater 212 is disposed proximate to a wash cup 216. In some examples, the induction heater 212 is coupled to the wash cup 216. For example, the induction heater 212 can be coupled to an interior of the wash cup 216. In the example of FIG. 2, at least a portion of the work piece 214 is disposed in the wash cup 216. In some examples, the work piece 214 is rinsed with fluid 218 (e.g., a liquid) before, during, and/or after being heated via the induction heater 212. The wash cup 216 collects the fluid 218.

The example induction heater control station 210 of FIG. 2 includes a power drive unit 220. In the example of FIG. 2, the power source 206 of the diagnostic instrument 202 provides power (e.g., in the form of direct current (DC)) to the power drive unit 220, as represented by arrow 222 of FIG. 2. The power received by the power drive unit 220 from the power source 206 is used to drive the induction heater 212 via drive signal(s),as represented by arrow 224 of FIG. 2. In some examples, the power drive unit 220 includes a DC-to-DC converter to convert the DC received from the power source 206 from one voltage level to another voltage level.

The example induction heater control station 210 of FIG. 2 includes an induction heater controller 226. The induction heater controller 226 includes a processor 227 to perform one or more control functions with respect to the induction heater 212 and/or the power drive unit 220. For example, the induction heater controller 226 generates one or more instruction(s) to activate and/or deactivate the induction heater 212 and monitors the status and/or performance of the induction heater 212 and/or other components of the induction heater control station 210 (e.g., the power drive unit 220). The power drive unit 220 provides power to the induction heater controller 226, as represented by arrow 228 of FIG. 2.

In the example system 200 of FIG. 2, the induction heater controller 226 is communicatively coupled with the processor 204 of the diagnostic instrument 202. The induction heater controller 226 includes a serial communication port to facilitate the transmission of data between the induction heater controller 226 and the processor 204 of the diagnostic instrument 202, as represented by arrow 230 of FIG. 2. For example, one or more user commands received via the GUI(s) 209 of the diagnostic instrument 202 can be transmitted to the induction heater controller 226 via the serial communication port 230. Also, the induction heater controller 226 can transmit, for example, performance data generated by monitoring the induction heater 212 to the diagnostic instrument 202 via the serial communication port 230. As another example, the timer 211 of the diagnostic instrument 202 transmits a trigger signal 232 to the induction heater controller 226 to provide timing control for one or more inductive heating events, such as activation and deactivation of the induction heater 212.

In addition to receiving power from the power drive unit 220 as disclosed above, the example induction heater controller 226 of FIG. 2 is communicatively coupled with the power drive unit 220. The example induction heater controller 226 provides one or more instructions 234 to the power drive unit 220 with respect to, for example, activation of the induction heater 212, a temperature at which to heat the work piece 214, etc. The example power drive unit 220 generates the drive signals 224 to drive the induction heater 212 based on the instruction(s) 234 received from the induction heater controller 226.

The example induction heater controller 226 also receives data from the power drive unit 220 with respect to, for example, performance of the induction heater 212. In the example of FIG. 2, the power drive unit 220 communicates data such as a status 236 of the induction heater 212, monitors data with respect to a current and/or a voltage at the induction heater 212, etc. Based on the data received from the power drive unit 220, the induction heater controller 226 can communicate, for example, a present/ready status signal 240 of the induction heater control station 210, a pass/fail status signal 242 with respect to a performance state of one or more components of the induction heater control station 210 such as the power drive unit 220 and/or the induction heater 212, and/or other signals containing data that can be used to control the induction heater control station 210 via the diagnostic instrument 202.

As disclosed below, in some examples, the induction heater controller 226 receives feedback 244 from the induction heater 212 with respect to, for example, a frequency at which a circuit of the induction heater 212 is oscillating. In some examples, the induction heater controller 226 receives analog feedback signals from the power drive unit 220 and/or the induction heater 212. The induction heater controller 226 converts the analog signals to digital data (e.g., via the processor 227) for analysis by the induction heater controller 226 and/or the processor 204 of the diagnostic instrument 202.

The example system 200 of FIG. 2 can include a pump 246 to control the flow of fluid 218 used to clean the work piece 214. Operation of the pump can be controlled by the power drive unit 220 based on, for example, the instructions 234 received from the processor 227 of the induction heater controller 227. In other examples, the pump 246 is controlled by the processor 204 of the diagnostic instrument 202. The instruction(s) can control, for instance, a speed at which the pump 216 pumps the fluid 218.

FIG. 3 is a block diagram of the example induction heater control station 210 of FIG. 2. The example induction heater control station 210 includes a heater board 300 (e.g., a printed circuit board) including one or more electrical components (e.g., circuits) coupled thereto. The example heater board 300 of FIG. 3 is operatively coupled to the induction heater controller 226.

In some examples, the heater board 300 includes the power drive unit 220 (e.g., the power drive unit 220 is mechanically and electrically coupled to the heater board 300). In other examples, the power drive unit 220 is separate from, but operatively coupled to, the heater board 300. As disclosed above, the power drive unit 220 receives power from the power source 206 of the diagnostic instrument 202 of FIG. 2. The power drive unit 220 delivers power to, for example, the induction heater controller 226, the other components of the heater board 300, etc.

The example heater board 300 of FIG. 3 is operatively coupled to the induction heater 212. The example induction heater 212 of FIG. 3 includes a tank circuit board 302 (e.g. a printed circuit board). In some examples, the tank circuit board 302 and the heater board 300 form a single board. In other examples, the heater board 300 and the tank circuit board 302 are separate boards.

The example tank circuit board 302 of FIG. 3 includes a tank circuit 304 (e.g., an inductance-capacitance or LC circuit) formed by a capacitor 306 and an inductor or work coil 308 (e.g., the coil 102 of FIG. 1). The work coil 308 includes an electrically conductive material such as a metal. The example power drive unit 220 provides electrical current 310 to and/or generates a voltage at the tank circuit 304. In some examples, the power drive unit 220 provides the current 310 to the tank circuit 304 via, for example, a shielded cable or a coaxial cable. As disclosed above with respect to FIG. 1, when the electrical current 310 flows through the work coil 308, a magnetic field (e.g., the magnetic field 106 of FIG. 1) is generated by the work coil 308. The magnetic field(s) can be used to heat the work piece 214 of FIG. 2 when the work piece 214 is disposed proximate to the work coil 308 (e.g., at least partially disposed in an opening of the work coil 308).

The example tank circuit board 302 of FIG. 3 includes a sense coil 312. In the example induction heater 212 of FIGS. 2 and 3, the sense coil 312 is wound around the work coil 308. The example sense coil 312 detects or senses the magnetic field(s) generated by the work coil 308. The sense coil 312 generates one or more sense signals 314 that are transmitted to the heater board 300. As disclosed below, the sense signal(s) 314 generated by the sense coil 312 are detected by frequency control circuitry 316 of the heater board 300 to drive the tank circuit 304 at a resonant frequency.

The example tank circuit board 302 includes a coil temperature sensor 318. The coil temperature sensor 318 detects a temperature of the work coil 308 and/or the sense coil 312 during, for example, generation of the magnetic field by the work coil 308. The coil temperature sensor 318 sends coil temperature data 320 to a temperature monitor 322 of the example heater board 300. In some examples, the temperature monitor 322 also collects temperature data with respect to the temperature of the heater board 300 and/or one or more electrical components of the board based on, for example, one or more temperature sensors coupled to the heater board 300. The temperature monitor 322 sends heater temperature data 323 with respect to the temperature of the work coil 308, the sense coil 312, the heater board 300, etc. to the induction heater controller 226.

The example heater board 300 of FIG. 3 also includes an electrical current monitor 324. The electrical current monitor 324 generates data with respect to the electrical current 310 being provided to the tank circuit 304 such as an amount of the current, a frequency of the current, etc. For example, the electrical current monitor 324 can detect overcurrent, or current exceeding a threshold current to be received by the tank circuit 304. The electrical current monitor 324 can detect changes in the current at the induction heater 212. The electrical current monitor 324 generates one or more current signals 325 based on the detection and transmits the current signal(s) 325 to the induction heater controller 226.

The example heater board 300 of FIG. 3 includes a voltage monitor 326. The voltage monitor 326 generates data with respect to a voltage in the tank circuit 304. In some examples, the voltage monitor 326 detects overvoltage, or voltage in the tank circuit 304 that exceeds a threshold limit of the tank circuit 304. The voltage monitor 326 can detect the voltage based on voltage measurements obtained from the tank circuit 304 (e.g., via a voltmeter). The electrical voltage monitor 326 can also detect changes in the voltage at the induction heater 212. The voltage monitor 326 generates one or more voltage signals 327 based on the detection and transmits the voltage signal(s) 327 to the induction heater controller 226.

As disclosed above, the example heater board 300 includes frequency control circuitry 316. The frequency control circuitry 316 sends one or more sense coil detection signals 328 to the example induction heater controller 226 of FIG. 3 based on the sense signals 314 generated by the sense coil 312 with respect to oscillation of the tank circuit 304. The example heater board 300 also includes a fixed frequency clock 330. As disclosed below, the frequency control circuitry 316 selectively enables the fixed frequency clock 330 to generate one or more fixed frequency signals or disables the fixed frequency clock 330 based on the sense signal(s) 314. The fixed frequency signals generated by the fixed frequency clock 330 cause the current 310 in the tank circuit 304 to oscillate at a fixed frequency.

Thus, the example induction heater controller 226 receives one or more signals 323, 325, 327, 328 from the circuitry of the example heater board 300. The induction heater controller 226 processes the data 323, 325, 327, 328 by, for example, converting the data from analog to digital, filtering the data, removing noise from the data, etc. The example induction heater controller 226 of FIG. 3 analyzes the data received from the heater board 300 and generates one or more instructions with respect to operation of the induction heater 212 and/or transmits data to the diagnostic instrument 202 of FIG. 2 for display to a user via the GUI(s) 209. Any of the functions of the example induction heater controller 226 of FIG. 3 disclosed herein can be performed by the processor 227 associated with the induction heater controller 226.

The example induction heater controller 226 of FIG. 3 includes a drive manager 332. The drive manager 332 generates the instruction(s) 234 that are transmitted to the power drive unit 220 and that cause the power drive unit 220 to generate, for example, the current 310 provided to the tank circuit 304 and/or the voltage to be generated at the tank circuit 304. The instruction(s) 234 generated by the drive manager 332 include, for example, an amount of current 310 to be provided to the tank circuit 304 and/or a voltage to be generated at the tank circuit 304, a duration for which the current 310 should be provide, etc. In some examples, the drive manager 332 generates the instruction(s) 234 based on reference data 334 stored in a database 336 of the induction heater controller 226. The reference data 334 can include data regarding, for example, a current threshold and/or a voltage threshold of the tank circuit 304, respective inductances of the work coil 308 and/or the sense coil 312, a capacitance of the capacitor 306, etc.

The example induction heater controller 226 of FIG. 3 includes a frequency manager 338. The frequency manager 338 processes the sense coil detection signals 328 generated by the frequency control circuitry 316. In some examples, the frequency manager 338 generates one or more frequency instructions 339 with respect to operation of the frequency control circuitry 316 and/or the fixed frequency clock 330 to cause the tank circuit 304 to selectively oscillate at resonant frequency or a fixed frequency, as disclosed below.

The example induction heater controller 226 of FIG. 3 includes a performance manager 340. The electrical current monitor 324 and/or the voltage monitor 326 send the respective current signal(s) 325 and/or the voltage signal(s) 327 indicative of, for example, a change in the current and/or the voltage at the induction heater 212 (e.g., at the tank circuit 304) to the performance manager 340. The example performance manager 340 generates one or more instructions for, for example, the power drive unit based on the monitoring of the current and/or voltage.

In some examples, the change(s) in voltage and/or current detected at the induction heater 212 are based on one or more of the properties 215 of the work piece 214 of FIG. 2 introduced into the induction heater 212. For example, the work piece 214 of FIG. 2 includes the first portion 217 and the second portion 219 having a diameter smaller than the diameter of the first portion 217 first diameter. In some examples, a thickness of a skin of the first portion 217 is greater than a thickness of the second portion 219. As disclosed above, the first and second portions 217, 219 of the work piece 214 can be selectively disposed proximate to the work coil 308 for heating via the magnetic field generated by the current 310 in the work coil 308. The presence of the first portion 217 and/or the second portion 219 relative to the work coil 308 can affect a load on the work coil 308.

In some examples, the electrical current monitor 324 of FIG. 3 detects a change in current at the tank circuit 304 when the second portion 219 having the thinner skin is disposed proximate to the work coil 308 as compared to the when the first portion 217 is disposed proximate to the work coil 308. For example, the electrical current monitor 324 can detect that the current 310 at the tank circuit 304 has dropped when the second portion 219 is proximate to the work coil 308 as compared to when the first portion 217 is disposed proximate to work coil 308. The electrical current monitor 324 generates the current signal(s) 325 with respect to the change in current at the induction heater 212 (e.g., the dropped current). In some examples, the voltage monitor 326 detects a change in voltage at the tank circuit 304 based on the load change at the work coil 308 due to the presence of the first portion 217 or the second portion 219 proximate to the work coil 308. The voltage monitor 326 generates the voltage signal(s) 327 with respect to the change in voltage detected at the induction heater 212.

The performance manager 340 of the induction heater controller 226 analyzes the current signal(s) 325 and/or the voltage signal(s) 327 relative to a temperature profile 342 for the work piece 214 stored in the database 336 of the example induction heater controller 226 of FIG. 3. The temperature profile 342 includes predefined data (e.g., provided via one or more user inputs to the processor 227 of the induction heater controller 226) with respect to a minimum temperature to heat the work piece 214 over a length of the work piece 214 to, for example, clean or sterilize the work piece 214. The temperature profile 342 is used by the performance manager 340 to determine power settings over time with respect to power to be provided to the induction heater 212 relative to one or more portions 217, 219 of the work piece 214 (e.g., loads) being heated by the induction heater 212.

The temperature profile 342 can be based on, for example, known data with respect to the properties 215 of the work piece 214 and a response of the work piece 214 to the magnetic field(s) based on the properties 215. The properties 215 of the work piece 214 result in load impedance variations at the induction heater 212 based on differences in, for example, skin thickness, diameter, etc., at the different portions 217, 219 of the work piece 214. The performance manager 340 uses the temperature profile 342 to control power delivered to the work piece 214 to heat the work piece 214 at each position of the work piece 214 relative to the induction heater 212 over time.

In some examples, the temperature profile 342 is a time-based profile with respect to a temperature at which the one or more portions 217, 219 of the work piece 214 are to be heated over time. In some examples, the temperature profile 342 is generated by the performance manager 340 of the induction heater controller 226 based on data previously collected during heating of the work piece 214 and/or one or more other work pieces (e.g., calibration or reference data). In some examples, the temperature profile 342 is based on one or more user inputs received via the GUI(s) 209 of the diagnostic instrument 202 with respect to, for example, voltage to be generated at the tank circuit 304 over time relative to a position of the work piece 214 at the induction heater 212. In in some examples, the temperature profile 342 represents an optimal temperature at which to heat the first portion 217 and/or the second portion 219 of the work piece 214 over time.

The example performance manager 340 of FIG. 3 directs to the drive manager 332 to provide the instruction(s) 234 to the power drive unit 220 based on the temperature profile 342. In some examples, the performance manager 340 determines the instruction(s) 234 to be sent to the power drive unit 220 based on a start time of the heating of the work piece 214 relative to a starting position of the work piece 214 in the induction heater 212 (e.g., whether the first portion 217 or the second portion 219 is to be heated first). In some examples, the performance manager 340 determines a position of the work piece 214 relative to the work coil 308 based on data from, for example, the processor 204 of the diagnostic instrument 202 regarding the movement and/or position of the robotic arm 221 and/or other positional data (e.g., a position data). The performance manager 340 determines additional instruction(s) 234 to be sent to the power drive unit 220 based on anticipated positions of the work piece 214 relative to the induction heater 212 as reflected in the temperature profile 342.

The performance manager 340 uses the temperature profile 342 to determine current and/or power to be provided to and/or the voltage to be generated at the induction heater 212 at different times during the heating of the work piece 214 at the induction heater 212. In some examples, the performance manager 340 of FIG. 3 analyzes the current signal(s) 325 and/or the voltage signal(s) 327 indicative of changes in current and/or voltage at the induction heater 212 relative to the temperature profile 342. Based on the analysis, the example performance manager 340 generates the instruction(s) 234 for the power drive unit 220 with respect to the current, voltage, and/or power at the induction heater 212 for different heat settings associated with the temperature profile 342.

For example, based on the current signal(s) 327, the performance manager 340 can detect a drop in current at the tank circuit 304 due to, for example, the second portion 219 of the work piece 214 having the thinner skin being disposed proximate to the work coil 308 as compared to the first portion 217 of the work piece 214. The performance manager 340 analyzes the temperature profile 342 to determine a higher temperature is required to heat the second portion 219 as compared to the first portion 217 due to the thinner skin of the work piece 214 (e.g., due to thinner portion 219 of the work piece heating less efficiently than the thicker portion 217 of the work piece 214). The example performance manager 340 generates the instruction(s) 234 for the power drive unit 220 to increase the current 310 provided to the tank circuit 304 when the second portion 219 is disposed proximate to the work 308 as compared the first portion 217 of the work piece 214.

In some examples, the DC-DC converter of the power drive unit 220 serves as a power source for generating voltage at the induction heater 212. In such example, the temperature profile 342 includes voltage values. The instruction(s) 234 sent to the power drive unit 220 include voltages to be generated at specific time intervals based on the temperature profile 342. In such examples, for a given heat setting (e.g., voltage), the power varies as a load impedance at the tank circuit 304 varies as result of movement of the work piece 214 between the first and second portions 217, 219 (e.g., via the robotic arm 221 of FIG. 2).

In other examples, the temperature profile 342 includes power values representative of desired power output values (e.g., wattage) at different times. In such examples, the performance manager 340 calculates the power based on the current data 325 from the electrical current monitor 324 and the voltage data 327 from the voltage monitor 326. The performance manager 340 adjusts the output voltage provided by the DC-DC converter to obtain the desired output power. In such examples, for a given heat setting (e.g., wattage), the power is substantially constant as the load impedance varies as result of movement of the work piece 214 between the first and second portions 217, 219 (e.g., via the robotic arm 221 of FIG. 2).

In other examples, the power drive unit 220 includes a fixed voltage source. In such examples, the output voltage is adjusted by duty cycles of FET gate signals of the power drive unit 220.

Thus, the example performance manager 340 of FIG. 3 provides for dynamic adjustment of the current and/or voltage at the tank circuit 304 and, as result, the power provided to the work piece 214 to heat the work piece 214. The performance manager 340 accounts for load impedance variations due to the properties 215 of the work piece 214 and the position of the work piece 214 relative to the induction heater 212 based on the monitoring of the current by the electrical current monitor 324 and/or the voltage by the voltage monitor 326. The example performance manager 340 uses the temperature profile 342 to respond to dynamic load variabilities resulting from the different portions 217, 219 of the work piece 214 to be heated. The current, voltage, and/or power adjustments implemented via the power drive unit 220 substantially improve performance of the induction heater 212 in view of the different properties 215 of the work piece 214 at different portions 217, 219 to efficiently heat the work piece 214.

The example induction heater controller 226 of FIG. 3 also includes a failure monitor 344. The failure monitor 344 analyzes the temperature data 323 generated by the temperature monitor 322 with respect to, example, potential overheating of one or more components of the heater board 300 (e.g., the frequency control circuitry 316) and/or the induction heater 212. The failure monitor 344 analyzes the current signal(s) 325 and/or the voltage signal(s) 327 with respect to overcurrent and/or overvoltage that could damage the induction heater 212 based, for example, an amount or frequency of the current 310 being provided to the tank circuit 304.

Based on the analysis of the temperature, current, and/or voltage data 323, 325, 327, the failure monitor 344 predicts whether one or more of the components of the induction heater control station 210 are likely to malfunction and/or fail (e.g., overheat, short). The failure monitor 344 can predict a performance status with respect to, for example, the induction heater 212 based on the reference data 334 stored in the database 336 of the induction heater controller 226. For example, the failure monitor 344 can detect overcurrent based on a predefined current threshold for the tank circuit 304 stored in the database 336.

If the failure monitor 344 determines that one or more components of the induction heater control station 210 are malfunctioning and/or failing and/or if the failure monitor 344 predicts that the one or more components are likely to fail, the failure monitor 344 generates one or more failure instructions 346. The failure instructions 346 can include, for example, instructions for the problematic component(s) to shut down, for other components to take over for the problematic component(s), etc. In some examples, the instruction(s) 234 sent to the power drive unit 220 include instructions to address potential failure due to, for example, overcurrent and/or overvoltage at the tank circuit 304 by reducing and/or stopping delivery of current to the tank circuit 304. In some examples, the failure monitor 344 stores historical data with respect to performance tracking of the heater board 300 and/or the tank circuit board 302 in the database 336. The historical data can be used by the failure monitor 344 to predict component failure.

The failure monitor 344 can also update the present/ready status signal 240 and/or the pass/fail status signal 242 (as shown in FIG. 2) transmitted to the processor 204 of the diagnostic instrument 202 based on analysis of the performance data of the induction heater control station 210. For example, if the failure monitor 344 detects an error with the induction heater 212, the failure monitor 344 can update the pass/fail status signal 242 to indicate the error state of the induction heater 212. The failure monitor 344 can generate other warnings for display, via, for example the GUI(s) 209 of the diagnostic instrument 202 with respect failure and/or historical data indicating changes in performance over time that may indicate future failures.

The example induction heater controller 226 of FIG. 3 includes a communicator 348 to transmit one or more of the instruction(s) 234, 339, 346 to the heater board 300. The communicator 348 can also transmit the present/ready status signal 240 and/or the pass/fail status signal 242 to the processor 204 of the diagnostic instrument 202.

Figure 4:
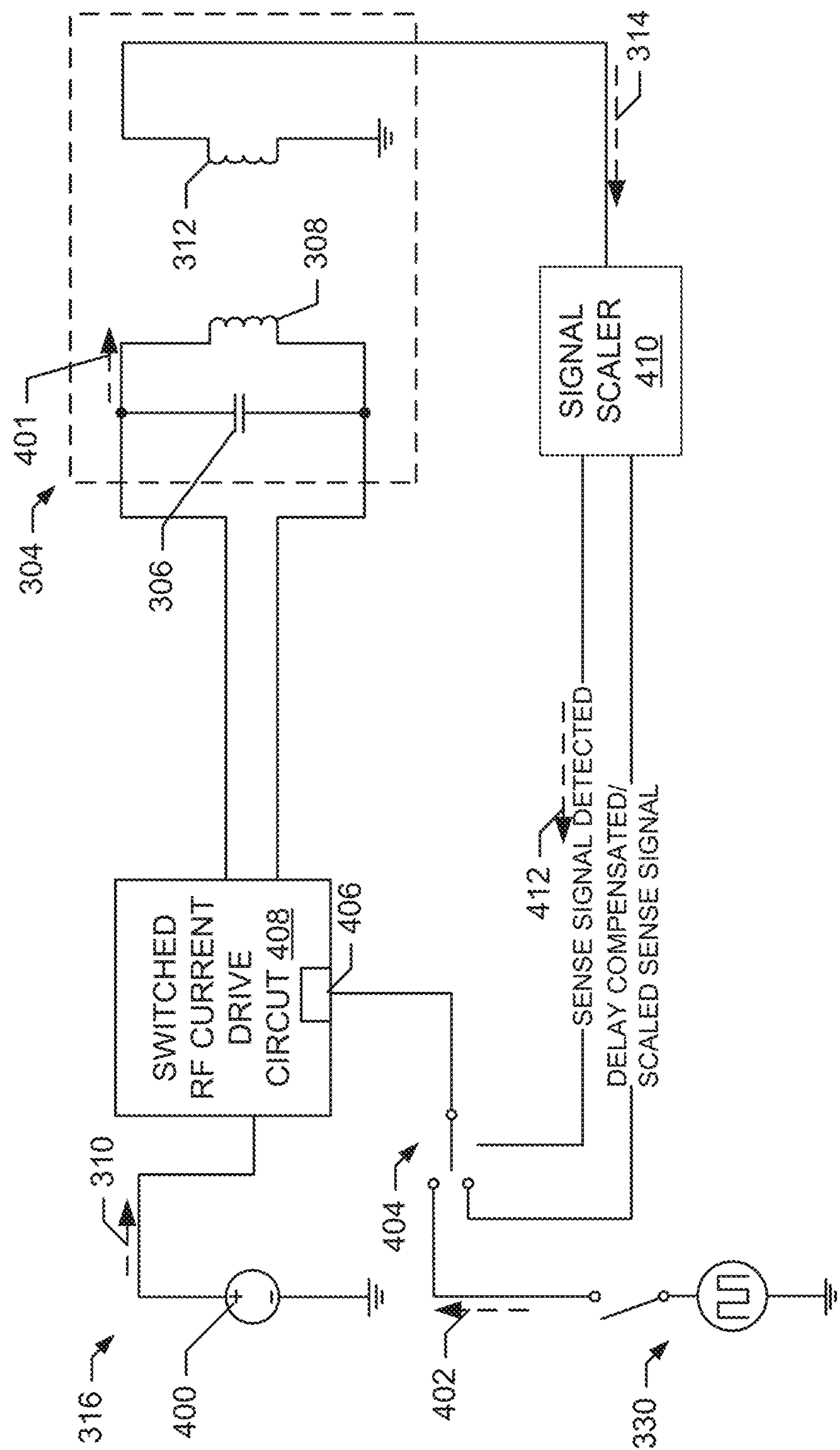
FIG. 4 is a schematic illustration of an example circuitry that may be used with the example induction heater station of FIG. 3.

FIG. 4 is a diagram of the example frequency control circuitry 316, the fixed frequency clock 330, and the tank circuit 304 of the example induction heater control station 210 of FIG. 3. As disclosed above with respect to FIG. 3, the tank circuit 304 includes the capacitor 306 and the work coil or inductor 308. The tank circuit 304 stores energy via an oscillating current between the capacitor 306 and the work coil 308. The oscillation of the current can result in energy losses in tank circuit 304. For example, energy can be lost due to the resistances of the work coil 308, the resonance of the capacitor 306, and the tank circuit board 302. Energy can also be lost as a result of the work piece 214 being heated by the magnetic field generated by the work coil 308. In the example of induction heater control station 210 of FIGS. 2-4, energy is provided to the tank circuit 304 in the form of an alternating current that is synchronized with the current already circulating in the tank circuit 304.

In the example of FIG. 4, the introduction of the work piece 214 in the tank circuit 304 changes an effective inductance of the work coil 308. Also, variations in the properties 215 of the work piece 214 such as density and/or a shape (e.g., at the different portions 217, 219) can also cause changes in the effective inductance of the work coil 308. Changes in effective inductance of the work coil 308 affect the resonant frequency of the tank circuit 304, or the frequency at which the current oscillates in the tank circuit 304 with the least energy loss. In the example of FIG. 4, the alternating current injected into the tank circuit has a frequency that is varied based on the changing effective inductive at the work coil 308 to maximize efficiency with respect to the synchronization of the current introduced into the tank circuit 304 with the current already circulating in the tank circuit 304. Such frequency adjustments enable the tank circuit 304 to oscillate at its resonant frequency and provide a dynamic response to load variations at the tank circuit 304 due to the introduction and/or manipulation of the work piece 214.

As disclosed above, the tank circuit 304 includes the sense coil 312 disposed proximate to (e.g., wound around) the work coil 308. The sense coil 312 sense the magnetic field generated by the work coil 308 (e.g., the magnetic field 106 of FIG. 1) and generates the sense signal(s) 314. The sense signal(s) 314 are used to synchronize the alternating current 310 that is injected into the tank circuit with current 401 already flowing in the tank circuit 304.

For example, at the beginning of a heat cycle (e.g., when the work piece 214 is disposed proximate to the work coil 308), a variable DC power supply 400 (e.g., of the power drive unit 220) is enabled by, for example, the instruction(s) 234 from the induction heater controller 226 of FIG. 3. The variable DC power supply 400 is set to a low power level by the drive manager 332 of the induction heater controller 226. The low power level setting of the variable DC power supply 400 limits the oscillation of the tank circuit 304 when the tank circuit 304 is oscillating at a frequency that may or may not be its resonant frequency, thereby limiting energy losses. In other examples, a power level of the variable DC power supply is not adjustable.

In the example of FIG. 4, the fixed frequency clock 330 is enabled by the example frequency manager 338 of the induction heater controller 226 of FIG. 3. The frequency manager 338 sets the fixed frequency clock 330 to generate a fixed frequency signal 402 proximate to the resonant frequency current of the tank circuit 304 (e.g., based on predefined data). The fixed frequency signal 402 travels via a switch 404 (e.g., a single pole, double throw or SPDT switch) to a SYNC input pin 406 of a switched resonant frequency (RF) current drive circuit 408. The fixed frequency signal 402 causes the current 310 supplied by the variable DC supply and the current 401 already in the tank circuit 304 to oscillate at a fixed frequency.

The example sense coil 312 of FIG. 4 senses induced oscillating fields in the work coil 308 as a result of the current flowing through the work coil 308 and generates the sense signal(s) 314. The example frequency control circuitry 316 of FIG. 4 includes a signal scaler 410. The signal scaler 410 scales the sense signal(s) 314 relative to the SYNC input pin 406 of the switched RF current drive circuit 408 (e.g., voltage scaling). The signal scaler 410 also applies a delay to the sense signal(s) 314 to optimize current synchronization to generate a scaled sense signal 412. In the example of FIG. 4, the signal scaler 410 includes circuitry to detect a validity of the sense signal(s) 314 with respect to, for example, scaling of the signal to predefined voltages, signal amplitude, etc.

When the signal scaler 410 detects the validity of the sense signal(s) 314 the switch 404 (e.g., the SPDT switch) is thrown such that the frequency control circuitry uses the sense signal(s) 314 to drive the SYNC input pin 406 of the switched RF current drive circuit 408 instead of the fixed frequency signal 402. As a result, the tank circuit 304 is released from being driven by the fixed frequency clock 330 and instead is driven at its resonant frequency with respect to the current 310 provided by the variable DC power supply 400 and the current 401 already circulating in the tank circuit 304.

In the example of FIG. 4, when the tank circuit 304 is driven at its resonant frequency, the variable DC power supply 400 is adjusted (e.g., based on instruction(s) 234 from the drive manager 332) to a high power level. Also, when the work piece 214 is disposed proximate to (e.g., inserted into) the work coil 308, the resonant frequency of the tank circuit 304 changes as the effective inductance of the work coil 308 changes due to the presence of the work piece 214. The sense coil 312 generates the sense signal(s) 314, which reflect the (e.g., modified) resonant frequency in the tank circuit 304. As a result, the current passing through the switched RF current drive circuit 408 is synchronized with current 401 in the tank circuit 304. Thus, the frequency control circuitry 316 dynamically responds to the introduction of the work piece 214 into the tank circuit 304 to enable the tank circuit 304 to be driven at its resonant frequency when the work piece 214 being heated by the work coil 308. The sense coil 312 and the frequency control circuitry 316 form a feedback loop that responds to variabilities in resonant frequency at the induction heater 212.

In the example FIG. 4, driving the tank circuit 304 at its resonant frequency substantially minimizes energy losses in the tank circuit 304. As a result, more energy is transferred to the work piece 214 to heat the work piece 214 as compared to if the tank circuit 304 oscillated at a fixed frequency that was not the resonant frequency of the tank circuit 304. Thus, the self-oscillation of the tank circuit 304 at its resonant frequency increases an efficiency of the induction heater 212. Also, in allowing the tank circuit 304 to oscillate at its resonant frequency rather than driving the tank circuit 304 to resonant at a fixed frequency, the example frequency control circuitry 316 substantially compensates for manufacturing variabilities and/or effect of aging of components of the induction heater control station 210, such as the work coil 308, the capacitor 306, the circuit boards 300, 302, etc. Manufacturing variabilities and/or age can change the oscillation behavior of the tank circuit 304 and, thus, result in inefficiencies if the tank circuit 304 were driven to oscillate only at a fixed frequency. Further, the example of FIG. 4 dynamically responds to load variabilities due to the introduction of the work piece 214 into the tank circuit 304 and/or exposure of different portions 217, 219 of the work piece 214 having different properties 215 to the induction heater 212. The example of FIG. 4 accommodates the resulting effects on the effective impedance of the work coil 308 and the resonant frequency of the tank circuit 304 due to the load variabilities by adjusting to the modified resonant frequency.

At the end of the heat cycle, the drive manager 332 of the induction heater controller 226 adjusts the variable DC power supply 400 to the low power setting and, after a predefined period of time (e.g., a delay), turns off the variable DC power supply 400. As a result, the energy in the tank circuit 304 diminishes. Over time, the sense coil 312 no longer generates a sense signal 314 large enough to be recognized as valid by the signal scaler 410. In such examples, the SYNC input pin 406 of the switched RF current drive circuit 408 is switched back to be driven by the fixed frequency clock 330. As a result, any remaining energy in the tank circuit 304 dissipates. After a predefined period of time (e.g., a delay), the drive manager 332 sends an instruction 234 for the fixed frequency clock 330 to be disabled.

Figure 5:
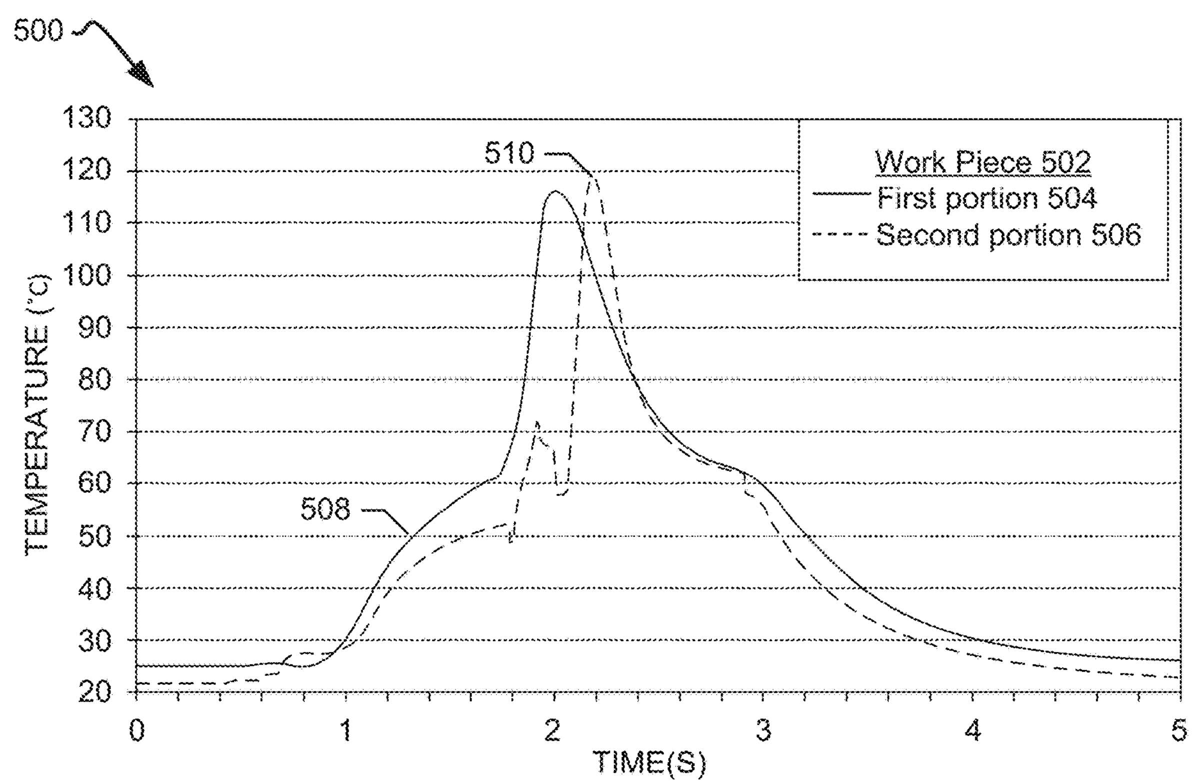
FIG. 5 is diagram illustrating an example temperature profile for inductively heating a work piece using the example system of FIG. 2.

FIG. 5 is an example diagram of a temperature profile 500 such as the temperature profile 342 of FIG. 3 for a work piece 502 having two or more portions with different properties, such as size, skin thickness, etc. The work piece 502 can be, for example, the work piece 214 of FIG. 3. The work piece 502 can include, for example, an aspiration and dispense device.

As illustrated in FIG. 5, the example temperature profile 500 includes a plot of temperature versus time for a first portion 504 of the example work piece 502 and a second portion 506 of the work piece 502. The first portion 504 of the work piece 502 can have, for example, a first thickness and the second portion 506 can have a second thickness different from the first thickness. The second portion 506 can have one or more other different properties from the first portion 504, such as a different size, cross-sectional shape, etc.

As illustrated in FIG. 5, the example temperature profile 500 includes a first temperature profile 508 for the first portion 504 with temperatures to heat the first portion 504 of the work piece 502 over time when the first portion 504 is disposed proximate to the work coil 308. The example temperature profile 500 includes a second temperature profile 510 for the second portion 506 with temperatures to heat the second portion 506 of the work piece 502 over time when the second portion 506 is disposed proximate to the work coil 308. In some examples, the first and second temperature profiles 508, 510 represent, for example, minimum temperatures at which to heat the respective first and second portion 504, 506 of the work piece 502 to clean (e.g., sterilize) the work piece 502. In other examples, the first and second temperature profiles 508, 510 represent optimal temperatures at which to heat the respective first and second portions 504, 506 to clean (e.g., sterilize) the work piece 502 in a predetermined time period. The optimal temperature data can be based on, for example, data collected from one or more prior inductive heating cycles of the work piece 502 and/or other work pieces. In some examples, the performance manager 340 of FIG. 3 uses the example temperature profile 500 to generate the instruction(s) 234 with respect to, for example, the current and/or power to be provided to and/or a voltage to be generated at the tank circuit 304 to heat the first and second portions 504, 506 of the work piece 502 at one or more predefined temperature or heat settings over time.

Figure 6:
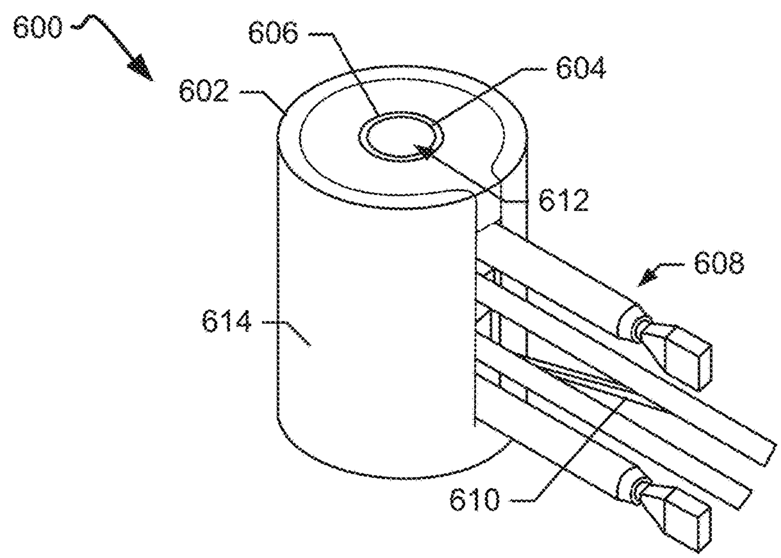
FIG. 6 is a perspective view of an example inductive heating coil that may be used with the example system of FIG. 2.

FIG. 6 is a perspective view of an example work coil 600 (e.g., the example work coil 308 of FIG. 3) that may be used with the induction heater 212 of the example induction heater control station 210 of FIGS. 2-4. The example work coil 600 includes a housing 602. In the example of FIG. 6, the housing 602 is a magnetic concentrator made of, for example, Ferrotron. The housing 602 includes a Litz wire 604 disposed therein. The Litz wire 604 includes a plurality of insulated wire strands woven together. In some examples, the Litz wire 604 is wrapped around a mandrel (e.g., a PEEK™ mandrel).

The example housing 602 of FIG. 6 also includes a magnetic wire 606 wound around the Litz wire 604. The magnetic wire 606 can include, for example, insulated copper wire. In the example of FIG. 6, the magnetic wire 606 serves as a sense coil (e.g., the sense coil 312 of FIGS. 3 and 4) for sensing a magnetic field generated by the work coil 600. In the example of FIG. 6, the windings of the Litz wire 604 and the magnetic wire 606 are in the same direction.

One or more electrical leads 608 can be coupled to the example work coil 600. The leads can be disposed in shrink tubing to protect the leads from the heat generated by the work coil 600. The example work coil 600 of FIG. 6 includes a thermistor 610, or a resistor that is used to measure a temperature of the housing 602 (e.g., the Ferrotron magnetic concentrator). The data generated by the thermistor 610 can be sent to, for example, the failure monitor 344 of the example induction heater controller 226 of FIG. 3.

The example work coil 600 can be selectively designed based on, for example, space constraints with respect to the induction heater control station 210 of the diagnostic instrument 202, a size of one or more work pieces to be heated by the work coil 600, etc. In some examples, variables such as wire cross-section shape, wire metal type, a number of turns of the wires, turn spacing, a height of work coil 600, a diameter of the work coil 600, a shape of the work coil 600, a resistance of the work coil 600, etc. are selectively chosen based on one or more intended uses of the work coil 600.

As illustrated in FIG. 6, the example work coil 600 includes an opening 612. In operation, a work piece (e.g., the work piece 214 of FIG. 2) is disposed in the opening 612 to be heated by the magnetic field(s) generated by the example work coil 600 of FIG. 6 when current flows through the work coil 600. Although the work piece does not touch or does not substantially touch the example work coil 600 during heating, the example work coil 600 is exposed to biological and/or chemical material(s) on the work piece. Also, in examples where the work piece is washed during heating, the example work coil 600 is exposed to wash fluid(s) (e.g., the fluid(s) 218 of FIG. 2). In some examples, at least some of the wash fluid(s) and/or biological/chemical material(s) may transfer to the work coil 600. Exposure to the wash fluid(s) and/or biological/chemical material(s) can corrode the work coil 600, which can damage the work coil 600.

To protect against corrosion, the example work coil 600 includes one or more coatings 614 applied to the housing 602. The coating(s) 614 can include, for example, surface treatment chemicals such as Chemtetall™ Oaktite® and/or ceramic coatings (e.g., ceramic coatings made by Cerakote™). Thus, the example work coil 600 of FIG. 6 includes protection against corrosion to increase an operational life of the work coil 600 and improve reliability of the work coil 600 in view of exposure to biological and/or chemical materials.

As disclosed above, the example induction heater control station 210 of FIG. 2 generates heat to clean a work piece, such as an aspiration and dispense device. In some examples, the heat can result in overheating of one or more components of the induction heater control station 210. The example induction heater control station 210 manages heat generated by the work coil (e.g., the work coil 308, 600 of FIGS. 3 and 6), one or more printed circuit boards (e.g., the heater board 300, the tank circuit board 302 of FIG. 3), and/or other electrical components of the printed circuit boards (e.g., the capacitor 306, the frequency control circuitry 316 of FIG. 3) through one or more heat management techniques. The heat management techniques employed by the induction heater control station 210 substantially reduce risks of, for example, the work coil shortening and/or waste heat damaging the electrical components of the printed circuit boards.

Figure 7:
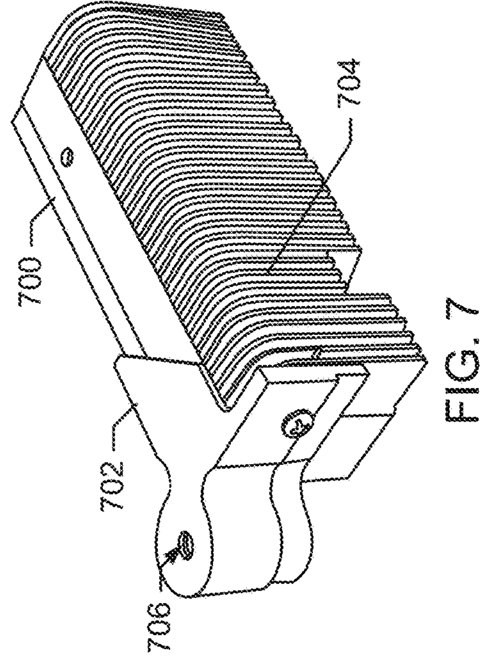
FIG. 7 is a perspective view of an example electromagnetic induction shield and an example heat sink for use in connection with the example system of FIG. 2.

For example, FIG. 7 illustrates an example tank circuit board 700 (e.g., the tank circuit board 302 of FIG. 3) including an electromagnetic interference (EMI) shield 702 and a heat sink 704. The EMI shield 702 includes a thermally conductive material (e.g., a metal) that substantially surrounds a work coil 706 (e.g., the work coils 308, 600 of FIGS. 2, 6). In some examples, the EMI shield 702 is coated with, for example, a coating including Teflon™. In some examples, the EMI of, for example, the induction heater 212 of FIG. 2 can exceed limits or regulations imposed by groups such as Underwriters Laboratories and/or government bodies such as the European Union. The example EMI shield 702 substantially reduces the EMI of the induction heater 212 so as to comply with one or more standards for regulatory approval (e.g., CE compliance).

The example heat sink 704 of FIG. 7 substantially reduces overheating of the work coil 706 and/or the tank circuit board 700 by directing waste heat away from the work coil 706 and/or the tank circuit board 700. In the example of FIG. 7, thermal energy is conducted through the conductors of the work coil 706, such as the Litz wire 604 of FIG. 6 (and, in some examples, the magnetic wire 606 of the sense coil of FIG. 6) and through one or more copper vias formed in, for example, the tank circuit board 700. The thermal energy is transferred to the heat sink 704. In some examples, thermal energy from the work coil 706 is also transferred to the heat sink via the thermally conductive material of the EMI shield 702. The example heat sink 704 transfers heat from, for example, the tank circuit board 700 to the ambient environment. In some examples, the heat sink transfers the heat to an interior of the diagnostic instrument in which the induction heater control station 210 is installed (e.g., the diagnostic instrument 202 of FIG. 2).

In some examples, the induction heater controller 226 of the example induction heater control station 210 of FIG. 2 reduces a duty cycle of the induction heater 212 (e.g., via the drive manager 332 and/or the performance manager 340 of FIG. 2) to manage the generation of waste heat. For example, the induction heater 212 can be activated so as to generate heat at a first temperature (e.g., based on the temperature profile 342, 500 of FIGS. 3 and 5) at a first power setting (e.g., watts) for a first predefined period of time, such as 4 seconds. The induction heater 212 can also be activated so as to generate heat at a second temperature at a second power setting (e.g., watts) that is higher than the first temperature for a second predefined period of time, such as 2 seconds. Although the first temperature generated over the first (e.g., longer) period of time and the second temperature generated over the second (e.g., shorter) period of time can both be used to heat the work piece, the lower temperature heat generated over the first (e.g., longer) period of time can take longer to dissipate. In the example of FIG. 7, the induction heater controller 226 instructs the induction heater 212 to generate heat over the shorter, second period of time to dissipate heat faster. Thus, the induction heater controller 226 reduces the duty cycle of the induction heater to more efficiently manage waste heat.

Thus, the heat management techniques employed by the induction heater control station 210 substantially reduce the risk of overheating the electrical components such as the coils, capacitor, etc. and, thus, improve performance of the induction heater control station 210. Further, the EMI shield 702, the heat sink 704, and/or the reduction in duty cycle substantially reduce the need for other mechanical modes of controlling and/or removing heat from the induction heater control station 210, thereby simplifying design considerations.

Figure 9:
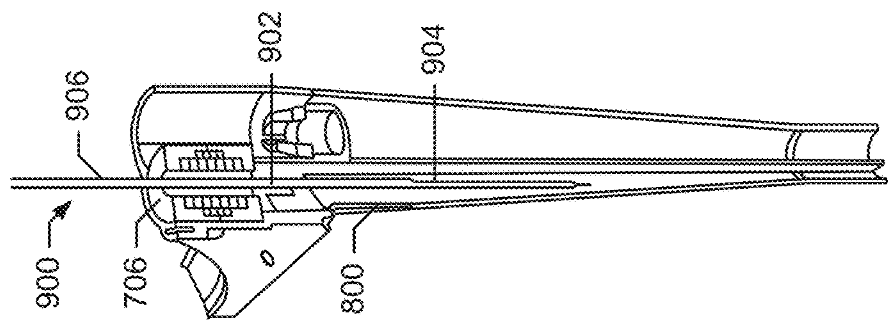
FIG. 9 is a cross-sectional view of the example first wash cup taken along the 1-1 line of FIG. 8.
Figure 8:
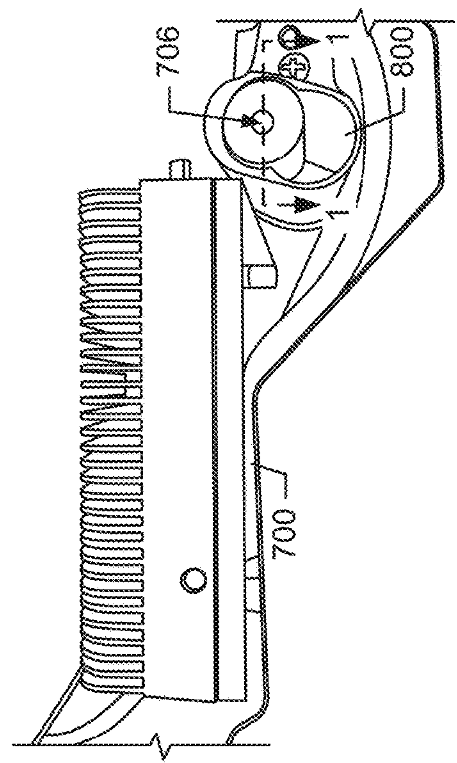
FIG. 8 is a top view of a first example wash cup for use in connection with the example system of FIG. 2.

FIG. 8 is a top, perspective view of the example tank circuit board 700 of FIG. 7 including the work coil 706 disposed in a wash cup 800 (e.g., the wash cup 216 of FIG. 2). FIG. 9 is a cross-sectional view of the example wash cup 800 and the work coil 706 taken along the 1-1 line of FIG. 8 including a work piece 900 (e.g., the work piece 214 of FIG. 2) disposed in the work coil 706. For illustrative purposes, the example EMI shield 702 of FIG. 7 is not shown in FIG. 8 or 9.

As disclosed above, in some examples, the work coil 706 is at least partially disposed in the wash cup 800 to facilitate, for example, washing of the work piece 900 before, during, and/or after inductive heating of the work piece 900 by the work coil 706 to help remove biological and/or chemical materials on the work piece 900. The wash cup 800 collects wash fluid (e.g., the fluid 218 of FIG. 2) used to rinse the work piece 900. The example wash cup 800 can include one or more openings or sections to accommodate and/or removably secure the work coil 706, electrical cables coupled to the work coil 706, etc., proximate to or substantially in the wash cup 800.

As illustrated in FIG. 9, a first portion 902 of the work piece 900 is disposed in the work coil 706 and is heated by the work coil 706. A second portion 904 of the work piece 900 is disposed in the wash cup 800 and a third portion 906 of the work piece 900 is not disposed in the wash cup 800. The work piece 900 can be selectively moved relative to the work coil 706 by, for example, the robotic arm 221 of FIG. 2, which may hold the third portion 906 of the work piece 900. As disclosed above, the induction heater control station 210 selectively adjusts the heat generated by the work coil 706 based on a temperature profile (e.g., the temperature profile 342, 500) to heat the first, second, and/or third portions 902, 904, 906 of the work piece 900 based on different properties of the respective portions, such as skin thickness, cross-section shape, diameter, etc.

Before, during, and/or after heating of the work piece 900, the wash buffer flows over one or more surfaces of the work piece 900 so as to wash away biological and/or chemical residue on the work piece 900. In some examples, the wash buffer flows over external and/or internal surfaces of the work piece 900.

In some examples, a phase change (e.g., liquid to vapor or gas) occurs with respect to the wash buffer used to clean the work piece during heating of the work piece due to the heat generated by the work coil 706. For instance, the pump 246 of the example system 200 of FIG. 2 establishes an elevated pressure to move fluid (e.g., a liquid such as the fluid 218 of FIG. 2) through the work piece 900, which, in this example, may be a probe having an opening extending along a length of the probe to receive the fluid. The fluid flow rate provided by the pump 246 can be substantially constant flow rate(s) or time-dependent flow rate(s). The elevation in pressure raises a saturation temperature of the fluid moving through the work piece 900. As a result of the heat generated during inductive heating via the work coil 706, the temperature of a material of at least a portion the work piece 900 (e.g., the portion surrounded by the work coil 706) increases due to the exposure of the work piece 900 to heat. The heat generated by the work coil 706 conducts through, for example, the walls of the work piece 900 (e.g., the probe). The heat is transferred to the fluid flowing through the work piece 900. As the work piece 900 is exposed to heat over time, the temperatures of the fluid can rise high enough to reach a saturation temperature for the fluid. When the fluid reaches its saturation temperature, a phase change of the fluid passing through the probe can occur. For example, the fluid passing through the portion of the work piece 900 disposed in the work coil 706 can undergo a phase change and become a saturated liquid-vapor mixture due the transfer of heat from the work coil through the walls of the work piece 900 to the fluid. When the fluid flows downstream, or past the region of the work piece 900 disposed in the work coil 706, the temperature of the fluid falls below the saturation temperature. As a result, the vapor in the liquid-vapor mixture condenses back to a liquid phase. Thus, the phase change of the fluid may be temporary based on the flow of fluid relative to the work coil 706.

When the phase change begins, bubbles form in the fluid moving through the work piece 900 (e.g., probe). The bubbles can be formed at or near the portion of the work piece 900 disposed in the work coil 706. The bubbles may be formed temporarily in the heated portion of the work piece 900 surrounded by the work coil. The formation, movement and collapse of a bubble locally alters the movement of the fluid passing through the work piece 900. The alteration of the movement of the fluid due to the bubble(s) alters magnitude and direction of shear stress in the fluid. Some inductive heating examples disclosed herein yield the formation, movement and collapse of a plurality bubbles, resulting in a plurality of (e.g., temporary) spikes in shear stress in the fluid and changes in shear stress direction that facilitate and/or enhance the cleaning of the work piece 900. Thus, in some examples disclosed herein, cleaning of the work piece 900 includes a combination of elevated temperatures and elevated liquid shear stresses. In some examples, the pump 246 of FIG. 2 generates pulsatile flow rates, which results in repeated drops in pressure to facilitate the phase change(s) and/or bubble effect(s).

As an example, the pump 246 of FIG. 2 may dispense fluid (e.g., liquid) at an average of 1.6 mL/s, which may produce an average pressure difference of 30 psig in the portion of the work piece 900 within the work coil 706. An example fluid can include a wash buffer including mostly water. As such, the wash buffer properties can be approximated as those of pure water. Assuming a 1 atm environment, the saturation temperature of water under this condition would be 134° C. An exterior surface temperature of a portion of the work piece 900 (e.g., the first portion 217 of the work piece 214 of FIG. 2) after preheating for 0.5 seconds at 270 W with 1.6 mL/s of fluid flow may be measured as, for example, 160° C. Accordingly, an inner surface temperature of the work piece 900 (e.g., defining an opening in the probe) is 154° C. Thus, the inner surface of the work piece 900 and, therefore, a layer of fluid at the inner surface is above the saturation temperature of water (and, thus, the wash buffer), which enables the phase change of the fluid.

The example wash cup 800 of FIGS. 8 and 9 can be made of a material that can withstand the heat generates by the work coil 706, such as Isoplast™ plastic. A shape, size, and/or other design factors of the wash cup 800 can be different than illustrated in FIGS. 8 and 9. For example, the design of the wash cup 800 can be selected based on the diagnostic instrument with which the wash cup 800 is to be used, the size of one or more work pieces to be cleaned, etc.

While an example manner of implementing the example system 200 is illustrated in FIGS. 2-9, one or more of the elements, processes and/or devices illustrated in FIGS. 2-9 may be combined, divided, re-arranged, omitted, eliminated and/or implemented in any other way. Further, the example diagnostic instrument 202, the example processors 204, 227, the example power source 206, the example display 208, the example GUI(s) 209, the example timer 211, the example induction heater control station 210, the example induction heater 212, the example power drive unit 220, the example induction heater controller 226, the example heater board 300, the example tank circuit board 302, the example capacitator 306, the example work coil 308, the example sense coil 312, the example frequency control circuitry 316, the example coil temperature sensor 318, the example temperature monitor 322, the example electrical current monitor 324, the example voltage monitor 326, the example fixed frequency clock 330, the example drive manager 332, the example database 336, the example frequency manager 338, the example performance manager 340, the example failure monitor 344, the example communicator 346, the example variable DC power supply 400, the example switched RF current drive circuit 408, the example signal scaler 410 and/or, more generally, the example system 200 of FIGS. 2-9 may be implemented by hardware, software, firmware and/or any combination of hardware, software and/or firmware. Thus, for example, any of the example diagnostic instrument 202, the example processors 204, 227, the example power source 206, the example display 208, the example GUI(s)

209, the example timer 211, the example induction heater control station 210, the example induction heater 212, the example power drive unit 220, the example induction heater controller 226, the example heater board 300, the example tank circuit board 302, the example capacitator 306, the example work coil 308, the example sense coil 312, the example frequency control circuitry 316, the example coil temperature sensor 318, the example temperature monitor 322, the example electrical current monitor 324, the example voltage monitor 326, the example fixed frequency clock 330, the example drive manager 332, the example database 336, the example frequency manager 338, the example performance manager 340, the example failure monitor 344, the example communicator 346, the example variable DC power supply 400, the example switched RF current drive circuit 408, the example signal scaler 410 and/or, more generally, the example system 200 of FIGS. 2-9 could be implemented by one or more analog or digital circuit(s), logic circuits, programmable processor(s), application specific integrated circuit(s) (ASIC(s)), programmable logic device(s) (PLD(s)) and/or field programmable logic device (s) (FPLD(s)). When reading any of the apparatus or system claims of this patent to cover a purely software and/or firmware implementation, at least one of the example diagnostic instrument 202, the example processors 204,227, the example power source 206, the example display 208, the example GUI(s) 209, the example timer 211, the example induction heater control station 210, the example induction heater 212, the example power drive unit 220, the example induction heater controller 226, the example heater board 300, the example tank circuit board 302, the example capacitator 306, the example work coil 308, the example sense coil 312, the example frequency control circuitry 316, the example coil temperature sensor 318, the example temperature monitor 322, the example electrical current monitor 324, the example voltage monitor 326, the example fixed frequency clock 330, the example drive manager 332, the example database 336, the example frequency manager 338, the example performance manager 340, the example failure monitor 344, the example communicator 348, the example variable DC power supply 400, the example switched RF current drive circuit 408, the example signal scaler 410 and/or, more generally, the example system 200 of FIGS. 2-9 is/are hereby expressly defined to include a tangible computer readable storage device or storage disk such as a memory, a digital versatile disk (DVD), a compact disk (CD), a Blu-ray disk, etc. storing the software and/or firmware. Further still, the example system 200 of FIGS. 2-9 may include one or more elements, processes and/or devices in addition to, or instead of, those illustrated in FIGS. 2-9, and/or may include more than one of any or all of the illustrated elements, processes and devices.

Figure 10:
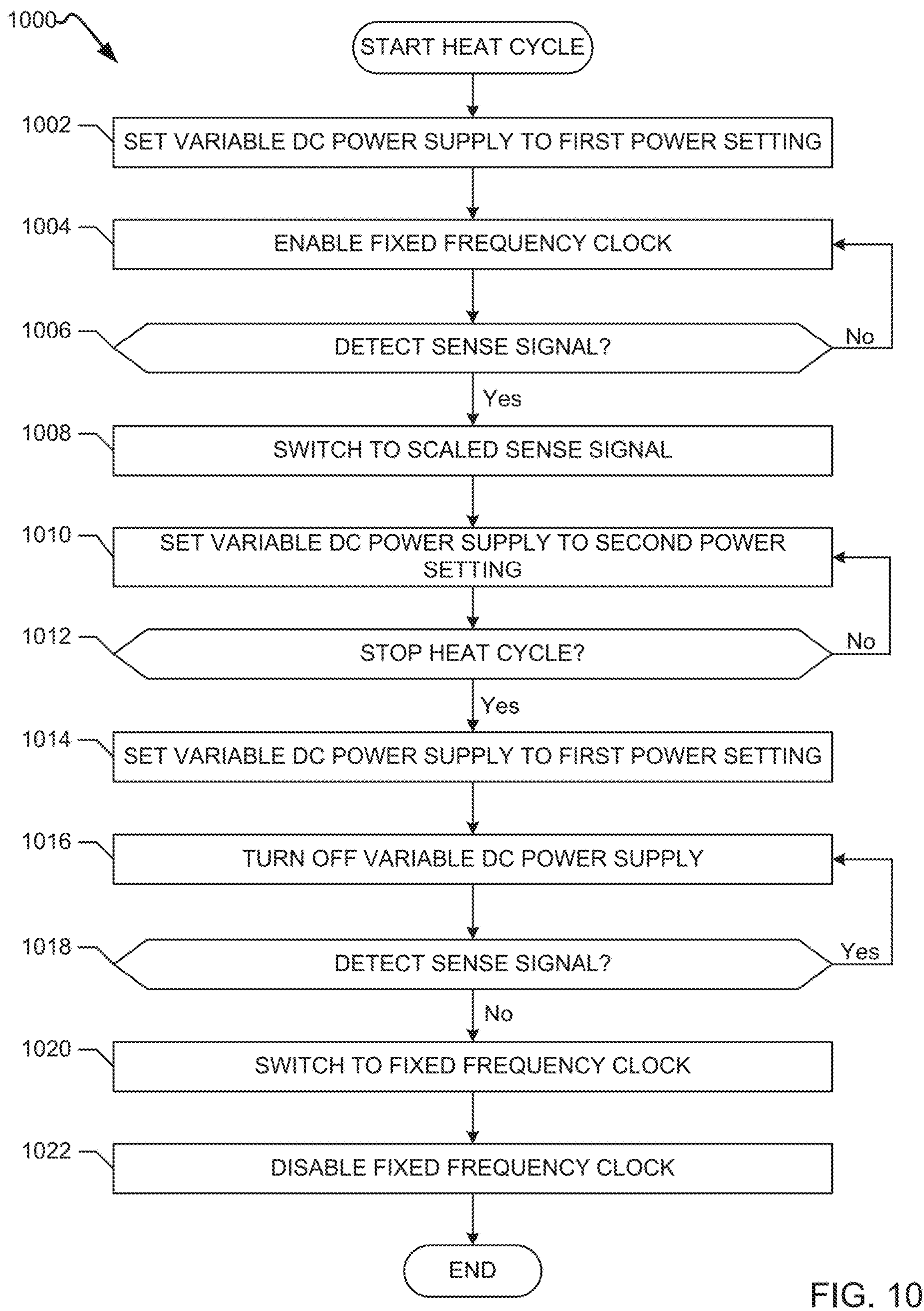
FIG. 10 is a flow diagram of an example method for causing a tank circuit to resonate at a natural frequency that can be used to implement the examples disclosed herein.
Figure 11:
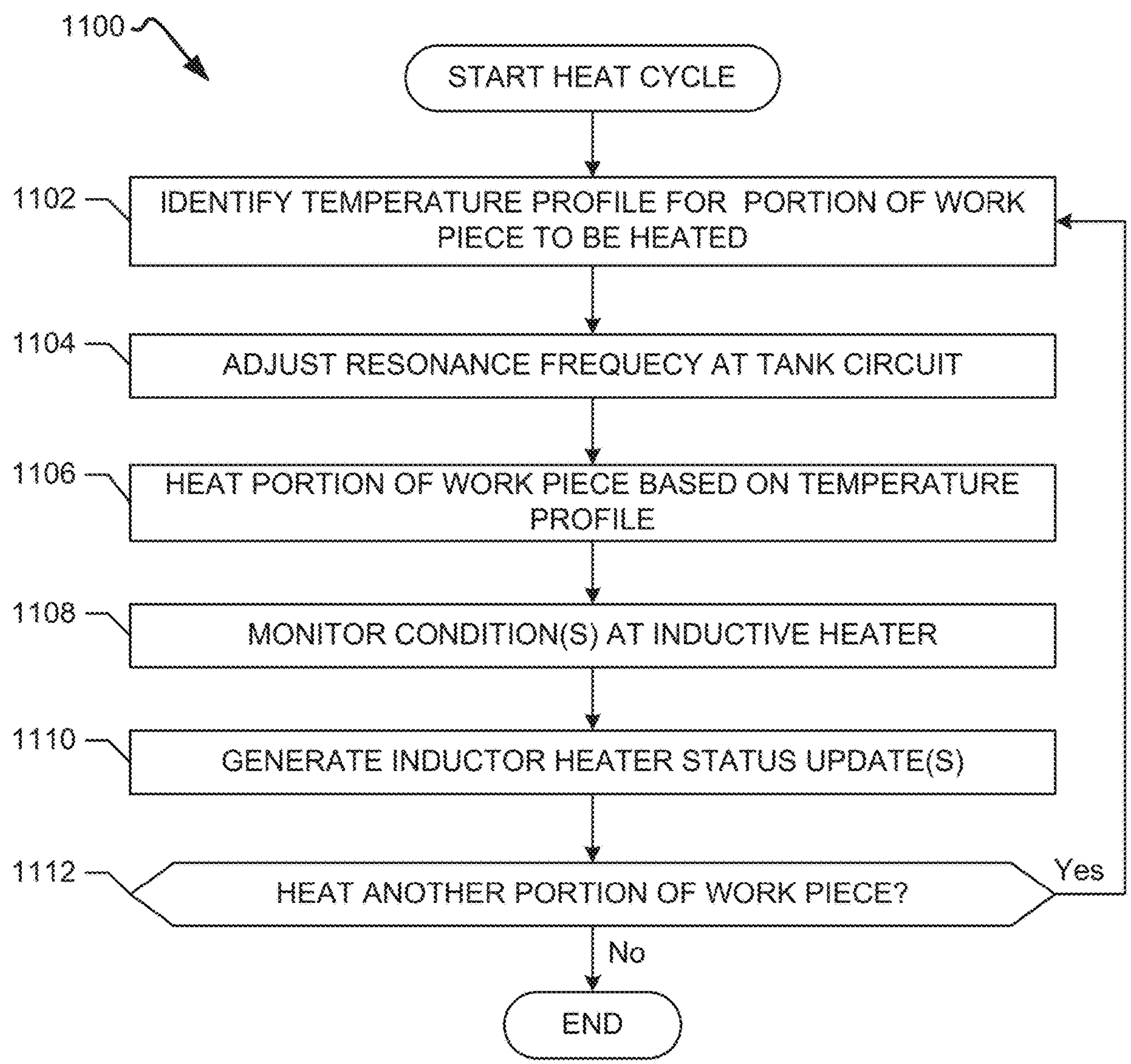
FIG. 11 is a flow diagram of an example method for inductively heating a work piece that can be used to implement the examples disclosed herein.

Flowcharts representative of example machine readable instructions for implementing the example system 200 of FIGS. 2-9 are shown in FIGS. 10 and 11. In these examples, the machine readable instructions comprise a program for execution by a processor such as the processor 227 shown in the example processor platform 1200 discussed below in connection with FIG. 12. The program may be embodied in software stored on a tangible computer readable storage medium such as a CD-ROM, a floppy disk, a hard drive, a digital versatile disk (DVD), a Blu-ray disk, or a memory associated with the processor 227, but the entire program and/or parts thereof could alternatively be executed by a device other than the processor 227 and/or embodied in firmware or dedicated hardware. Further, although the example program is described with reference to the flowchart illustrated in FIGS. 10 and 11 many other methods of implementing the example system 200 may alternatively be used. For example, the order of execution of the blocks may be changed, and/or some of the blocks described may be changed, eliminated, or combined.

As mentioned above, the example processes of FIGS. 10 and 11 may be implemented using coded instructions (e.g., computer and/or machine readable instructions) stored on a tangible computer readable storage medium such as a hard disk drive, a flash memory, a read-only memory (ROM), a compact disk (CD), a digital versatile disk (DVD), a cache, a random-access memory (RAM) and/or any other storage device or storage disk in which information is stored for any duration (e.g., for extended time periods, permanently, for brief instances, for temporarily buffering, and/or for caching of the information). As used herein, the term tangible computer readable storage medium is expressly defined to include any type of computer readable storage device and/or storage disk and to exclude propagating signals and to exclude transmission media. As used herein, "tangible computer readable storage medium" and "tangible machine readable storage medium" are used interchangeably. Additionally or alternatively, the example processes of FIGS. 10 and 11 may be implemented using coded instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and to exclude transmission media. As used herein, when the phrase "at least" is used as the transition term in a preamble of a claim, it is open-ended in the same manner as the term "comprising" is open ended.

FIG. 10 depicts an example flow diagram representative of an example method 1000 for causing a tank circuit of an induction heater such as the tank circuit 304 of the induction heater 212 of FIGS. 2 and 3 to resonate at a resonant frequency during a heat cycle of the induction heater. The example method 1000 may be implemented by, for example, the induction heater controller 226 of FIGS. 2 and 3 (e.g., the processor 227), the frequency control circuitry 316 of FIGS. 3 and 4, etc.

The example method 1000 includes setting a variable DC power supply to a first power setting at a start of a heat cycle (block 1002). The start of the heat cycle can include when a work piece such as the work piece 214 of FIG. 2 is disposed proximate to the work coil for heating. In some examples, the start of the heat cycle is determined based on one or more user inputs to the induction heater controller 226. The drive manager 332 of the example induction heater controller 226 of FIG. 3 can send instruction(s) 234 to the power drive unit 220 to set the variable DC power supply 400 of FIG. 4 to a low power setting to substantially limit energy losses at the tank circuit 304 whether or not the tank circuit 304 is resonating at its resonant frequency.

The example method 1000 includes enabling a fixed frequency clock (block 1004). For example, the fixed frequency clock 330 can be enabled by the example frequency manager 338 of the example induction heater controller 226 of FIG. 3. Enabling the fixed frequency clock 330 generates the fixed frequency signal 402, which travels to the SYNC input pin 406 of the switched RF current drive circuit 408. The example switched RF current drive circuit 408 drives the tank circuit 304 to oscillate at a fixed frequency.

The example method 1000 includes detecting a sense signal (block 1006). For example, when current flows through the work coil 308 of FIG. 3, the work coil 308 generates a magnetic field (e.g., the magnetic field 106 of FIG. 1). The example sense coil 312 of FIG. 3 detects the magnetic field and generates the sense signal 314. The sense signal 314 can be detected by the example signal scaler 410 of the frequency control circuitry 316 of FIG. 4.

If the sense signal 314 is not detected, the example method 1000 continues with driving the tank circuit 304 to resonate at a fixed frequency via the current provided to the tank circuit 304 (e.g., block 1004). If the signal scaler 410 detects the sense signal 314, the example method 1000 continues with switching to drive the tank circuit to resonate at its resonant frequency via a scaled sense signal (block 1008).

For example, the signal scaler 410 generates the scaled sense signal 412 by scaling the sense signal 314 relative to SYNC input pin 406 (e.g., voltage scaling). The signal scaler 410 applies a delay to the sense signal 314 to optimize the synchronization of the current provided to the tank circuit 304 and the current 401 already flowing through the tank circuit 304. In the example method 1000, the frequency manager 338 instructs the frequency control circuitry 316 to throw a switch (e.g., the SPDT switch 404 of FIG. 4) to use the scaled sense signal 412 to drive the switched RF current drive circuit 408 instead of the fixed frequency signal 402.

The example method 1000 includes setting the variable DC power supply to a second power setting (block 1010). For example, the drive manager 332 of the example induction heater controller 226 of FIG. 3 can send instruction(s) 234 to the power drive unit 220 to set the variable DC power supply 400 of FIG. 4 to a high power setting (as compared to the low setting set at block 1002).

The example method 1000 continues with enabling the tank circuit 304 to resonate at its resonant frequency until a determination is made that the heat cycle has ended (block 1012). In some examples, the example method 1000 adjusts the current provided to the tank circuit 304 based on the sense signal(s) 314 generated during inductive heating of the work piece 214 to enable to the tank circuit 304 to continue to resonate at its resonant frequency despite load variabilities at the work coil 308 due to the work piece 214.

In some examples, the induction heater controller 226 determines that the heat cycle is to end based on the current signal(s) 325 received from the electrical current monitor 324 indicating a change in current flow at the work coil 308. In some examples, changes in current flow at the work coil 308 can indicate that the work piece 214 or a portion thereof has been moved out of the magnetic field. In some examples, the induction heater controller 226 determines that the heat cycle is to end based on one or more user inputs.

If the heat cycle is to end, the example method 1000 includes setting the setting a variable DC power supply to the first (e.g., low) power setting (e.g., via the drive manager 332) (block 1014). After a delay, the example method 1000 includes turning off the variable DC power supply (block 1016).

The example method 1000 of FIG. 10 includes a determination of whether the sense signal is detected (block 1018). For example, after the variable DC power supply is turned off, the energy in the tank circuit 304 dissipates over time and the sense coil 312 no longer generates sense signal(s) 314 that are recognized by the signal scaler 410. If the sense signal(s) 314 are no longer detect, the example method 1000 includes switching the SYNC input pin 406 of the switched RF current drive circuit 408 to be driven by the fixed frequency clock 330 (e.g., via the drive manager 332) (block 1020). After a period of time, the example method 1000 includes disabling the fixed frequency clock 330 to end the heat cycle of the induction heater 212 (block 1022).

FIG. 11 depicts an example flow diagram representative of an example method 1100 for inductively heating a work piece such as the work piece 214, 502 of FIGS. 2 and 5 via an induction heater, such as the induction heater 212 of FIG. 2. The example method 1100 may be implemented by, for example, the induction heater controller 226 of FIGS. 2 and 3 (e.g., the processor 227).

The example method 1100 of FIG. 11 begins at the start of a heat cycle, which may be determined by, for example, a user input to the induction heater controller 226. The user input to begin the heat cycle can cause the drive manager 332 to instruct the power drive unit 220 to provide, for example, current to the tank circuit 304 of the example induction heater 212.

The example method 1100 includes identifying a temperature profile for a portion of a work piece to be heated (block 1102). For example, the performance manager 340 of the induction heater controller 226 can identify the temperature profile 342, 500 stored in the database 336 of FIG. 3. The example temperature profile 342, 500 includes one or more heat settings for the induction heater 212 with respect to the portion 217, 219, 504, 506 of the work piece 214, 502 to be heated. In some examples, the performance manager 340 identifies the temperature profile 342, 500 for the portion based on one or more user inputs defining, for example, the properties 215 of the portion 217, 219, 504, 506 to be heated (e.g., size, skin thickness). In other examples, the performance manager 340 identifies the temperature profile 342 based on a position of the work piece 214, 502 relative to the induction heater 212 (e.g., based on movement by the robotic arm 221 of the diagnostic instrument 202). In other examples, the performance manager 340 identifies the temperature profile 342, 500 based on change in current and/or voltage at the induction heater 212 as respectively detected by the electrical current monitor 324 and/or the voltage monitor 326. In some such examples, changes such as drop in current can indicate that a different portion 217, 219, 504, 506 of the work piece 214, 502 is disposed proximate to the work coil 308 for heating.

The example method 1100 includes adjusting a resonance frequency at a tank circuit of the induction heater (block 1104). The adjusting of the resonance frequency of the tank circuit can be performed substantially as disclosed above with respect to the example method 1000 of FIG. 10. For example, as disclosed above, the induction heater controller 226 and the frequency control circuitry 316 enable the tank circuit 304 to resonate at its resonant frequency during generation of the magnetic field by the work coil 308 based on sense signal(s) 314 generated by the sense coil 312. The oscillation of the tank circuit 304 at its resonant frequency provides for efficient transfer of heat to the work piece 214, 502.

The example method 1100 includes heating the portion of the work piece based on the temperature profile (block 1106). For example, the induction heater 212 of the FIGS. 2-4 can heat the portion 217, 219, 504, 506 of the work piece 214, 502 for a predefined duration of time at one or more heat settings based on the temperature profile 342, 500. In some examples, the induction heater controller 226 generates the instruction(s) 234 to adjust a current and/or power provided to the tank circuit 304 and/or a voltage generated at the tank circuit 304 achieve the heat settings of the temperature profile 342, 500 for the portion 217, 219, 504, 506 to be heated.

The example method 1100 includes monitoring one or more conditions at the induction heater (block 1108). For example, the example failure monitor 344 analyzes the temperature data 323 received from the temperature monitor 322, the current data 325 received from the electrical current monitor 324, and/or the voltage data 327 received from the voltage monitor 326 of FIG. 3. Based on the analysis, the example failure monitor 344 detects if any of the components of the induction heater 212 have failed and/or predicts if any of the components are likely to fail. For example, the failure monitor 344 identifies conditions that may result in, for example, overheating of the work coil 308, shorting of one or more components of the frequency control circuitry 316, etc. In some examples, the failure monitor 344 compares the data 323, 325, 327 to reference data 334 stored in the database 336 of FIG. 3 with respect to, for example, threshold currents and/or voltage for the tank circuit 304. The failure monitor 344 tracks performance data obtained from the induction heater 212 to identify and/or predict one or more failures at the induction heater control station 210.

The example method 1100 includes generating one or more induction status updates (block 1110). For example, the failure monitor 344 can generate one or more instructions 346 to stop operation of the induction heater 212 if the failure monitor 344 predicts that the work coil 308 is likely to overheat. In some examples, the failure monitor 344 instructs the power drive unit 220 to adjust the current provided to the induction heater 212 in view of the failure predictions and/or performance tracking by the failure monitor 344. In some examples, the failure monitor 344 generates the present/ready data 240 and/or the pass/fail data 242 for display via the GUI(s) 209 of the example diagnostic instrument 202 based on the predictions.

The example method 1100 includes a determination of whether another portion of the work piece is to be heated (block 1112). If another portion of the work coil is to be heated, the example method 1100 returns to identifying the temperature profile 342, 500 for the other portion to be heated (e.g., block 1102). The example method 1100 adjusts the resonance frequency at the tank circuit based on changes to the resonant frequency due to load variabilities at the tank circuit to efficiently heat the portion(s) of the work piece (e.g., blocks 1104, 1106). The load variabilities can result from the introduction of the other portion into the tank circuit having one or more different properties than the portion previously being heated by the induction heater. If another portion of the work piece is not to be heated, then the example method 1100 ends.

Figure 12:
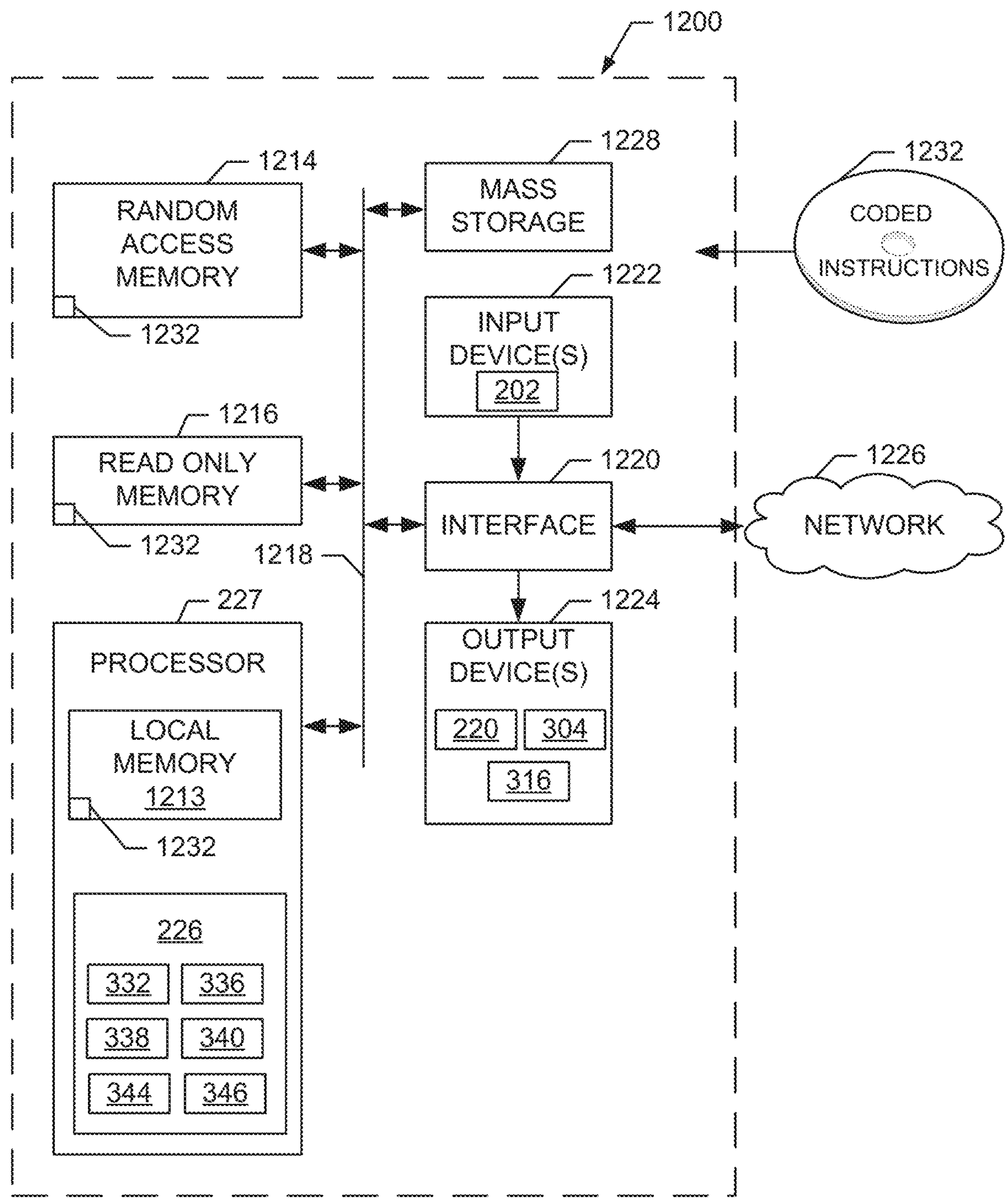
FIG. 12 is a diagram of an example processor platform for use with the examples disclosed herein.

FIG. 12 is a block diagram of an example processor platform 1200 capable of executing the instructions of FIGS. 10 and 11 to implement the example system 200 of FIGS. 2-9. The processor platform 1200 can be, for example, a server, a personal computer, a mobile device (e.g., a cell phone, a smart phone, a tablet such as an iPad™), a personal digital assistant (PDA), an Internet appliance, the medical diagnostic instrument 202 or any other type of computing device.

The processor platform 1200 of the illustrated example includes the processor 227. The processor 227 of the illustrated example is hardware. For example, the processor 227 can be implemented by one or more integrated circuits, logic circuits, microprocessors or controllers from any desired family or manufacturer.

The processor 227 of the illustrated example includes a local memory 1213 (e.g., a cache). The processor 227 of the illustrated example is in communication with a main memory including a volatile memory 1214 and a non-volatile memory 1216 via a bus 1218. The volatile memory 1214 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 1216 may be implemented by flash memory and/or any other desired type of memory device. Access to the main memory 1214, 1216 is controlled by a memory controller.

The processor platform 1200 of the illustrated example also includes an interface circuit 1220. The interface circuit 1220 may be implemented by any type of interface standard, such as an Ethernet interface, a universal serial bus (USB), and/or a PCI express interface.

In the illustrated example, one or more input devices 1222 are connected to the interface circuit 1220. The input device(s) 1222 permit(s) a user to enter data and commands into the processor 227. The input device(s) can be implemented by, for example, an audio sensor, a microphone, a camera (still or video), a keyboard, a button, a mouse, a touchscreen, a track-pad, a trackball, isopoint, a voice recognition system, and/or the medical diagnostic instrument 202.

One or more output devices 1224 are also connected to the interface circuit 1220 of the illustrated example. The output devices 1224 can be implemented, for example, by display devices (e.g., a light emitting diode (LED), an organic light emitting diode (OLED), a liquid crystal display, a cathode ray tube display (CRT), a touchscreen, a tactile output device, a printer and/or speakers), the power drive unit 220, the frequency control circuitry 316, the induction heater 212. The interface circuit 1220 of the illustrated example, thus, typically includes a graphics driver card, a graphics driver chip or a graphics driver processor.

The interface circuit 1220 of the illustrated example also includes a communication device such as a transmitter, a receiver, a transceiver, a modem and/or network interface card to facilitate exchange of data with external machines (e.g., computing devices of any kind) via a network 1226 (e.g., an Ethernet connection, a digital subscriber line (DSL), a telephone line, coaxial cable, a cellular telephone system, etc.).

The processor platform 1200 of the illustrated example also includes one or more mass storage devices 1228 for storing software and/or data. Examples of such mass storage devices 1228 include floppy disk drives, hard drive disks, compact disk drives, Blu-ray disk drives, RAID systems, and digital versatile Coded instructions 1232 to implement the example methods of FIGS. 10 and 11 may be stored in the mass storage device 1228, in the volatile memory 1214, in the non-volatile memory 1216, and/or on a removable tangible computer readable storage medium such as a CD or DVD.

From the foregoing, it will be appreciated that the above systems, methods, and apparatus provide for control and monitoring of performance of an induction heater to reduce biological carryover by one or more work pieces (e.g., probes) via inductive heating. Examples disclosed herein account for manufacturing variabilities and/or aging of electrical components of the induction heater by enabling the tank circuit to resonate at its resonant frequency rather than a fixed frequency. Further, examples disclosed herein dynamically response to load variabilities at the induction heater due to, for example, the introduction of the work piece into the induction heater, positioning of the work piece relative to the induction heater, and properties of different portions of the work piece to be heated. Some such examples adjust current provided to the tank circuit of the induction heater to respond to changes in the resonant frequency of the tank circuit as a result of the presence of the work piece. Some disclosed examples provide for improved reliability of the induction heater through waste heat management techniques that reduce the risk of overheating and/or through predictive failure analysis. Examples disclosed herein can be implemented with a diagnostic instrument (e.g., a chemical analyzer) to provide a system that efficiently analyzes samples and conveniently cleans tools used to perform the analysis without requiring a separate cleaning instrument.

Although certain example methods, apparatus and articles of manufacture have been disclosed herein, the scope of coverage of this patent is not limited thereto. On the contrary, this patent covers all methods, apparatus and articles of manufacture fairly falling within the scope of the claims of this patent.

What is claimed is:

1. A system comprising:
- an induction heater including a tank circuit, the tank circuit including a work coil and a sense coil, the sense coil to detect a magnetic field generated by the work coil and to output signals in response to the detection;
- a power drive unit;
- machine-readable instructions; and
- at least one processor circuit to execute the machine-readable instructions to:
  - cause the tank circuit to switch from oscillating at a fixed frequency to oscillating at a resonant frequency in response to the signals; and
  - cause the power drive unit to adjust power provided to the induction heater in response to the tank circuit oscillating at the resonant frequency.

2. The system of claim 1, wherein one or more of the at least one processor circuit is to:
- identify a change in a current or a voltage at the induction heater in response to a presence of a work piece in the magnetic field; and
- instruct the power drive unit to adjust the power in response to the identification of the change in the current or the voltage.

3. The system of claim 2, wherein one or more of the at least one processor circuit is to identify the change in the current or the voltage in response to a change in position of the work piece relative to the work coil.

4. The system of claim 2, wherein one or more of the at least one processor circuit is to instruct the power drive unit to adjust the power based on a temperature profile for the work piece.

5. The system of claim 1, wherein one or more of the at least one processor circuit is to:
- instruct the power drive unit to cause power having a first power level to be provided to the induction heater when the tank circuit is oscillating at the fixed frequency; and
- instruct the power drive unit to cause power having a second power level to be provided to the induction heater when the tank circuit is oscillating at the resonant frequency, the second power level different than the first power level.

6. The system of claim 5, wherein one or more of the at least one processor circuit is to instruct the power drive unit to cause power having a third power level to be provided to the induction heater when the tank circuit is oscillating at the resonant frequency in response a change in the signals, the third power level different than the first power level and the second power level.

7. The system of claim 6, wherein the change in the signals is indicative of a presence of a work piece relative to the work coil.

8. The system of claim 1, wherein the power drive unit is to adjust the power by adjusting a current provided to or a voltage generated at the induction heater.

9. An apparatus comprising:
- at least one memory;
- machine-readable instructions; and
- at least one processor circuit to execute the machine-readable instructions to:
  - cause a tank circuit of an induction heater to switch from oscillating at a fixed frequency to oscillating at a resonant frequency in response to signals output by a sense coil of the tank circuit, the sense coil to output the signals based on a magnetic field generated by a work coil of the tank circuit;
  - detect a change in the signals output by the sense coil in response to a presence of a work piece relative to the work coil; and
  - cause a power drive unit to modify a power output at the induction heater in response to the change in the signals output by the sense coil.

10. The apparatus of claim 9, wherein one or more of the at least one processor circuit is to detect the change in the signals in response to a change in position of at least a portion of the work piece relative to the work coil.

11. The apparatus of claim 9, wherein one or more of the at least one processor circuit is to detect the change in the signals in response to a change in a property of a portion of the work piece proximate to the work coil.

12. The apparatus of claim 9, wherein one or more of the at least one processor circuit is to cause the power drive unit to modify the power output based on an amount of heat to be generated by the induction heater.

13. The apparatus of claim 9, wherein one or more of the at least one processor circuit is to cause the power drive unit to modify the power output by adjusting a current provided to or a voltage generated at the induction heater.

14. The apparatus of claim 9, wherein one or more of the at least one processor circuit is to cause the tank circuit to switch from oscillating at the fixed frequency to oscillating at the resonant frequency by controlling a switch.

* * * * *